(12) United States Patent
Zablocki et al.

(10) Patent No.: US 6,573,264 B1
(45) Date of Patent: Jun. 3, 2003

(54) HETEROARYL ALKYL PIPERAZINE DERIVATIVES

(75) Inventors: Jeff Zablocki, Mountain View, CA (US); Prabha N. Ibrahim, Mountain View, CA (US); Kevin Shenk, Palo Alto, CA (US); Elfatih Elzein, Fremont, CA (US); Venkata Palle, Mountain View, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 0 days.

(21) Appl. No.: 09/694,155

(22) Filed: Oct. 23, 2000

(51) Int. Cl.⁷ ............... A61K 31/496; A61K 31/498; C07D 401/12; C07D 403/12; C07D 413/12; C07D 417/12
(52) U.S. Cl. ............ 514/249; 514/253.01; 514/253.06; 514/254.02; 514/254.09; 544/354; 544/360; 544/363; 544/368; 544/373
(58) Field of Search ................ 544/368, 373, 544/354, 360, 363; 514/254.02, 254.09, 249, 253.01, 253.06

(56) References Cited

U.S. PATENT DOCUMENTS 4,567,264 A * 1/1986 Kluge et al. ................ 544/400
5,472,707 A * 12/1995 Samuels et al.
5,506,229 A * 4/1996 Dow et al. .................. 514/255

FOREIGN PATENT DOCUMENTS

| EP | 0 407 780 | 1/1991 |
|---|---|---|
| WO | WO 01/62749 | 8/2001 |

OTHER PUBLICATIONS

McCormick, et al. "Ranolazine: A Novel Metabolic Modulator for the Treatment of Angina", Gen Pharmac., vol. 30, No. 5, pp. 639–645, (1998).

* cited by examiner

Primary Examiner—Emily Bernhardt
(74) Attorney, Agent, or Firm—McDonnell Boehnen Hulbert & Berghoff

(57) ABSTRACT

Novel compounds of the general formula:

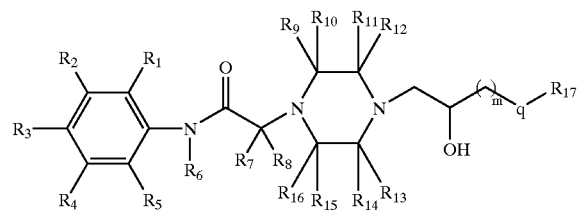

and pharmaceutically acceptable acid addition salts thereof, wherein the compounds are useful in therapy to protect skeletal muscles against damage resulting from trauma or to protect skeletal muscles subsequent to muscle or systemic diseases such as intermittent claudication, to treat shock conditions, to preserve donor tissue and organs used in transplants, in the treatment of cardiovascular diseases including atrial and ventricular arrhythmias, Prinzmetal's (variant) angina, stable angina, and exercise induced angina, congestive heart disease, and myocardial infarction.

41 Claims, No Drawings

HETEROARYL ALKYL PIPERAZINE DERIVATIVES

BACKGROUND OF THE INVENTION

1. Field of the Invention

The present invention is concerned with piperazine derivatives, therapeutic dosage forms including one or more of the derivatives, and methods for treating diseases in mammals, and in particular, in a human in a therapy selected from the group including protecting skeletal muscles against damage resulting from trauma, protecting skeletal muscles subsequent to muscle or systemic diseases such as intermittent claudication, to treat shock conditions, to preserve donor tissue and organs used in transplants, and to treat cardiovascular diseases including atrial and ventricular arrhythmias, Prinzmetal's (variant) angina, stable angina, and exercise induced angina, congestive heart disease, and myocardial infarction.

2. Description of the Art

U.S. Pat. No. 4,567,264, the specification of which is incorporated herein by reference, discloses a class of substituted piperazine compounds that includes a compound known as ranolazine, (±)-N-(2,6-dimethylphenyl)-4-[2-hydroxy-3-(2-methoxyphenoxy)-propyl]-1-piperazineacetamide, and its pharmaceutically acceptable salts, and their use in the treatment of cardiovascular diseases, including arrhythmias, variant and exercise-induced angina, and myocardial infarction.

U.S. Pat. No. 5,506,229, which is incorporated herein by reference, discloses the use of ranolazine and its pharmaceutically acceptable salts and esters for the treatment of tissues experiencing a physical or chemical insult, including cardioplegia, hypoxic or reperfusion injury to cardiac or skeletal muscle or brain tissue, and for use in transplants. In particular, ranolazine is particularly useful for treating arrhythmias, variant and exercise-induced angina, and myocardial infarction by partially inhibiting cardiac fatty acid oxidation. Conventional oral and parenteral ranolazine formulations are disclosed, including controlled release formulations. In particular, Example 7D of U.S. Pat. No. 5,506,229 describes a controlled release formulation in capsule form comprising microspheres of ranolazine and microcrystalline cellulose coated with release controlling polymers.

Despite the important discovery that ranolazine is a very useful cardiac therapeutic agent, there remains a need for compounds that are partial fatty acid oxidation inhibitors that have a half-life greater than ranolazine and that have activities as least similar to ranolazine.

SUMMARY OF THE INVENTION

This invention includes novel heteroaryl alkyl piperazine derivatives that are partial fatty acid oxidation inhibitors with good therapeutic half-lives.

This invention also includes novel substituted piperazine compounds that can be administered to a mammal to protect skeletal muscles against damage resulting from trauma, to protecting skeletal muscles subsequent to muscle or systemic diseases such as intermittent claudication, to treat shock conditions, to preserve donor tissue and organs used in transplants, and to treat cardiovascular diseases including atrial and ventricular arrhythmias, Prinzmetal's (variant) angina, stable angina, and exercise induced angina, congestive heart disease, and myocardial infarction.

This invention includes a class of substituted piperazine compounds having the formula:

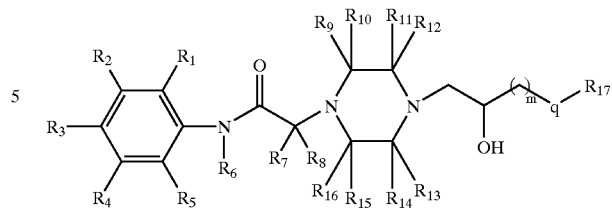

wherein m=1, 2, or 3;

q=NH, O, or S;

$R^1$, $R^2$, $R^3$, $R^4$ and $R^5$ are each independently selected from the group consisting of hydrogen, halo, $NO_2$, $CF_3$, CN, $OR^{20}$, $SR^{20}$, $N(R^{20})_2$, $S(O)R^{22}$, $SO_2R^{22}$, $SO_2N(R^{20})_2$, $NR^{20}CO_2R^{22}$, $NR_{20}CON(R^{20})_2$, $COR^{20}$, $CO_2R^{20}$, $CON(R^{20})_2$, $NR^{20}SO_2R^{22}$, $C_{1-15}$ alkyl, $C_{2-15}$ alkenyl, $C_{2-15}$ alkynyl, heterocyclyl, aryl, and heteroaryl, wherein the alkyl and aryl substituent are optionally substituted with 1 substituent selected from the group consisting of halo, $NO_2$, $CF_3$, CN, $OR^{20}$, $SR^{20}$, $N(R^{20})_2$, $S(O)R^{22}$, and $SO_2R^{22}$;

$R^6$, $R^7$ and $R^8$ each independently selected from the group consisting of hydrogen or $C_{1-3}$ alkyl;

$R^9$, $R^{10}$, $R^{11}$, $R^{12}$, $R^{13}$, $R^{14}$, $R^{15}$ and $R^{16}$ are each independently selected from the group consisting of hydrogen, $CO_2R^{20}$, $CON(R^{20})_2$, $C_{1-4}$ alkyl, or aryl wherein the alkyl and aryl substituents are optionally substituted with 1 substituent selected from the group consisting of halo, $CF_3$, CN, $OR^{20}$, $N(R^{20})_2$, $CO_2R^{20}$, $CON(R^{20})_2$ or aryl, wherein $R^9$ and $R^{10}$ may together form a carbonyl, or $R^{11}$ and $R^{12}$ may together form a carbonyl, or $R^{13}$ and $R^{14}$ may together form a carbonyl, or $R^{15}$ and $R^{16}$ may together form a carbonyl or $R^{11}$ and $R^{13}$ or $R^9$ and $R^{15}$ or $R^9$ and $R^{11}$ or $R^{11}$ and $R^{15}$ or $R^9$ and $R^{13}$ may join together to form a ring including from 1 to 3 carbon atoms;

$R^{17}$ is heteroaryl that is optionally substituted with from 1 to 3 substituents selected from the group consisting of hydrogen, halo, $NO_2$, $CF_3$, CN, $OR^{20}$, $SR^{20}$, $N(R^{20})_2$, $S(O)R^{22}$, $SO_2R^{22}$, $SO_2N(R^{20})_2$, $NR^{20}CO_2R^{22}$, $NR^{20}CON(R^{20})_2$, $COR^{20}$, $CO_2R^{20}$, $CON(R^{20})_2$, $NR^{20}SO_2R^{22}$, $C_{1-15}$ alkyl, $C_{2-15}$ alkenyl, $C_{2-15}$ alkynyl, heterocyclyl, aryl, or heteroaryl, wherein the alkyl and aryl substituents are optionally substituted with 1 substituent selected from the group consisting of halo, $NO_2$, $CF_3$, CN, $OR^{20}$, $SR^{20}$, $N(R^{20})_2$, $S(O)R^{22}$, or $SO_2R^{22}$;

$R^{20}$ is selected from the group consisting of H, $C_{1-15}$ alkyl, aryl, or heteroaryl, wherein the alkyl and aryl substituents are optionally substituted with 1 substituent selected from the group consisting of halo, alkyl, mono- or dialkylamino, alkyl CN, —O—$C_{1-6}$ alkyl, or $CF_3$; and $R^{22}$ is selected from the group consisting of $C_{1-15}$ alkyl, aryl, or heteroaryl, wherein the alkyl and aryl substituents are optionally substituted with 1 substituent selected from the group consisting of halo, alkyl, monoalkylamino, dialkylamino, alkyl amide, aryl amide, heteroaryl amide, CN, O—$C_{1-6}$ alkyl, $CF_3$, or heteroaryl.

In another embodiment, this invention is a substituted piperazine compound selected from the group consisting of N-(2,6-dimethyl-phenyl)-2-(4-{2-hydroxy-3-[2-(3-trifluoromethylphenyl)-benzoxazol-5-yloxy]-propyl}-piperazin-1-yl)acetamide, 2-{4-[3-(benzothiazol-2-yloxy)-2-hydroxy-propyl]-piperazin-1-yl}-N-(2,6-dimethylphenyl) acetamide, N-(2,6-dimethylphenyl)-2-{4-[2-hydroxy-3-(2-methyl-benzothiazol-5-yloxy)-propyl]-piperazin-1-yl}acetamide,4-(3-{4-[(2,6-dimethylphenylcarbamoyl)-methyl]-piperazin-1-yl}-2-hydroxy-propoxy)-1H-indole-2-carboxylic acid amide, 2-{4-[3-(benzothiazol-6-yloxy)2-hydroxy-propyl]-piperazin-1-yl}-N-(2,6-dimethyl-phenyl)-acetamide, N-(2,6-dimethylphenyl)-2-{4-[2-hydroxy-3-(2-methyl-benzothiazol-6-yloxy)-propyl]-piperazin-1-yl}aceamide, N-(2,6-dimethylphenyl)-2-{4-[2-hydroxy-3-(2-methyl-benzothiazol-5-yloxy)-propyl]-3,5-dimethyl-piperazine-1-yl}acetamide, 2-{4-[2-hydroxy-3-(2-methyl-benzothiazol-5-yloxy)-propyl]-piperazin-1-yl}-N-(4-hydroxy-phenyl)acetamide, N-(2,6-dimethylphenyl)-2-{4-[2-hydroxy-3-(2-phenyl-benzothiazol-5-yloxy)-propyl]-piperazin-1-yl}acetamide, N-(2,6-dimethylphenyl)-2-{4-[2-hydroxy-3-(2-phenyl-benzoxazol-5-yloxy)-propyl]-piperazin-1-yl}acetamide, N-(2,6-dimethylphenyl)2-{4-[2-hydroxy-3-(2-phenyl-benzothiazol-7-yloxy)-propyl]-piperazin-1-ylacetamide, N-(2,6-dimethylphenyl)-2-{4-[2-hydroxy-3-(2-methyl-benzothiazol-5-yloxy)-propyl]-2-oxo-piperazin-1-yl}acetamide, N-(2,6-dimethylphenyl)-2-{4-[2-hydroxy-3-(2-methyl-benzoxazol-5-yloxy)-propyl]-piperazin-1-yl}acetamide, N-(2,6-dimethylphenyl)-2-(4-{2-hydroxy-3-[2-(4-trifluoromethyl-phenyl)-benzoxazol-5-yloxy]-propyl}-piperazin-1-yl)acetamide, N-(2,6-dimethylphenyl)-2-{4-[2-hydroxy-3-(quinoxalin-2-yloxy)-propyl]-piperazin-1-yl}acetamide, N-(2,6-dimethylphenyl)-2-{4-[2-hydroxy-3-(pyridin-3-yloxy)-propyl]-piperazin-1-yl}acetamide, N-(2,6-dimethylphenyl)-2-{4-[2-hydroxy-3-(quinolin-4-yloxy)-propyl]-piperazin-1-yl}acetamide, N-(2,6-dimethylphenyl)-2-{4-[2-hydroxy-3-(isoquinolin-5-yloxy)-propyl]-piperazin-1-yl}acetamide, N-(2,6-dimethylphenyl)-2-{4-[2-hydroxy-3-(quinolin-6-yloxy)-propyl]-piperazin-1-yl}acetamide, N-(2,6-dimethylphenyl)-2-{4-[2-hydroxy-3-(2-methyl-quinolin-7-yloxy)-propyl]-piperazin-1-yl}acetamide, 2-{4-[3-(benzothiazol-2-ylamino)-2-hydroxypropyl]piperazinyl}-N-(2,6-dimethylphenyl)acetamide, 2-(4-[3-(benzoxazol-2-ylamino)-2-hydroxypropyl]piperazinyl}-N-(2,6-dimethylphenyl)acetamide and mixtures thereof.

In yet another embodiment, this invention is a method for administering one or more composition of this invention to a mammal in a treatment selected from the group consisting of protecting skeletal muscles against damage resulting from trauma, protecting skeletal muscles subsequent to muscle or systemic diseases such as intermittent claudication, to treat shock conditions, to preserve donor tissue and organs used in transplants, and to treat cardiovascular diseases including atrial and ventricular arrhythmias, Prinzmetal's (variant) angina, stable angina, and exercise induced angina, congestive heart disease, and myocardial infarction.

DETAILED DESCRIPTION OF THE INVENTION

A class of substituted piperazine compounds having the following formula:

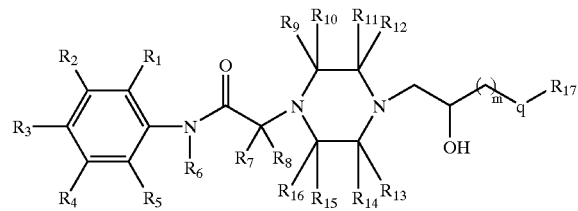

wherein m=1, 2, or 3;
q=NH, O, or S;
$R^1$, $R^2$, $R^3$, $R^4$ and $R_5$ are each independently selected from the group consisting of hydrogen, halo, $NO_2$, $CF_3$, CN, $OR^{20}$, $SR^{20}$, $N(R^{20})_2$, $S(O)R^{22}$, $SO_2R^{22}$, $SO_2N(R^{20})_2$, $NR^{20}CO_2R^{22}$, $NR^{20}CON(R^{20})_2$, $COR^{20}$, $CO_2R^{20}$, $CON(R^{20})_2$, $NR^{20}SO_2R^{22}$, $C_{1-15}$ alkyl, $C_{2-15}$ alkenyl, $C_{2-15}$ alkynyl, heterocyclyl, aryl, and heteroaryl, wherein the alkyl and aryl substituent are optionally substituted with 1 substituent selected from the group consisting of halo, $NO_2$, $CF_3$, CN, $OR^{20}$, $SR^{20}$, $N(R^{20})_2$, $S(O)R^{22}$, and $SO_2R^{22}$;

$R^6$, $R^7$ and $R^8$ each independently selected from the group consisting of hydrogen or $C_{1-3}$ alkyl;

$R^9$, $R^{10}$, $R^{11}$, $R^{12}$, $R^{13}$, $R^{14}$, $R^{15}$ and $R^{16}$ are each independently selected from the group consisting of hydrogen, $CO_2R^{20}$, $CON(R^{20})_2$, $C_{1-4}$ alkyl, or aryl wherein the alkyl and aryl substituents are optionally substituted with 1 substituent selected from the group consisting of halo, $CF_3$, CN, $OR^{20}$, $N(R^{20})_2$, $CO_2R^{20}$, $CON(R^{20})_2$ or aryl, wherein $R^9$ and $R^{10}$ may together form a carbonyl, or $R^{11}$ and $R^{12}$ may together form a carbonyl, or $R^{13}$ and $R^{14}$ may together form a carbonyl, or $R^{15}$ and $R^{16}$ may together form a carbonyl or $R^{11}$ and $R^{13}$ or $R^9$ and $R^{15}$ or $R^9$ and $R^{11}$ or $R^{11}$ and $R^{15}$ or $R^9$ and $R^{13}$ may join together to form a ring including from 1 to 3 carbon atoms;

$R^{17}$ is heteroaryl that is optionally substituted with from 1 to 3 substituents selected from the group consisting of hydrogen, halo, $NO_2$, $CF_3$, CN, $OR^{20}$, $SR^{20}$, $N(R^{20})_2$, $S(O)R^{22}$, $SO_2R^{22}$, $SO_2N(R^{20})_2$, $NR^{20}CO_2R^{22}$, $NR^{20}CON(R^{20})_2$, $COR^{20}$, $CO_2R^{20}$, $CON(R^{20})_2$, $NR^{20}SO_2R^{22}$, $C_{1-15}$ alkyl, $C_{2-15}$ alkenyl, $C_{2-15}$ alkynyl, heterocyclyl, aryl, or heteroaryl, wherein the alkyl and aryl substituents are optionally substituted with 1 substituent selected from the group consisting of halo, $NO_2$, $CF_3$, CN, $OR^{20}$, $SR^{20}$, $N(R^{20})_2$, $S(O)R^{22}$, or $SO_2R^{22}$;

$R^{20}$ is selected from the group consisting of H, $C_{1-15}$ alkyl, aryl, or heteroaryl, wherein the alkyl and aryl substituents are optionally substituted with 1 substituent selected from the group consisting of halo, alkyl, mono- or dialkylamino, alkyl, CN, —O—$C_{1-6}$ alkyl, or $CF_3$; and $R^{22}$ is selected from the group consisting of $C_{1-15}$ alkyl, aryl, or heteroaryl, wherein the alkyl and aryl substituents are optionally substituted with 1 substituent selected from the group consisting of halo, alkyl, monoalkylamino, dialkylamino, alkyl amide, aryl amide, heteroaryl amide, CN, O—$C_{1-6}$ alkyl, $CF_3$, or heteroaryl.

In a preferred embodiment, q=NH or O.
In a preferred embodiment, $R^1$, $R^2$, $R^3$, $R^4$ and $R^5$ are each independently selected from the group consisting of hydrogen, halo, $CF_3$, CN, $OR^{20}$, $SR^{20}$, $N(R^{20})_2$, $SO_2N(R^{20})_2$, $CO_2R^{20}$, $CON(R^{20})_2$, $C_{1-8}$ alkyl, $C_{2-8}$ alkenyl, $C_{2-8}$ alkynyl, heterocyclyl, aryl, or heteroaryl, wherein the alkyl and aryl substituents are optionally substituted with 1 substituent selected from the group consisting of halo, $NO_2$, $CF_3$, CN, $OR^{20}$, $SR^{20}$, $N(R^{20})_2$, $S(O)R^{22}$, or $SO_2R^{22}$. In another preferred embodiment, $R^1$, $R^2$, $R^3$, $R^4$ and $R^5$ are each independently selected from the group consisting of hydrogen, halo, $CF_3$, $OR^{20}$, $C_{1-5}$ alkyl, $C_{2-5}$ alkenyl, or $C_{2-5}$ alkynyl, wherein the alkyl substituent is optionally substituted with $CF_3$. In yet another preferred embodiment, $R^1$, $R^2$, $R^3$, $R^4$ and $R^5$ are each independently selected from the group consisting of hydrogen, halo, $CF_3$, $OR^{20}$, or $C_{1-3}$ alkyl wherein the alkyl substituent is optionally substituted with $CF_3$. More preferably $R^1$, $R^2$, $R^3$, $R^4$ and $R^5$ are each independently selected from the group consisting of hydrogen, $CF_3$, $OR^{20}$, or $C_{1-2}$ alkyl, with hydrogen, $OR^{20}$, or methyl being more preferred and hydrogen or methyl being most preferred.

In a preferred embodiment, $R^6$, $R^7$ and $R^8$ each independently selected from the group consisting of hydrogen or $C_{1-3}$ alkyl and most preferably hydrogen or methyl.

In a preferred embodiment, $R^9$, $R^{10}$, $R^{11}$, $R^{12}$, $R^{13}$, $R^{14}$, $R^{15}$ and $R^{16}$ are each independently selected from the group consisting of hydrogen, $CON(R^{20})_2$, $C_{1-4}$ alkyl, or wherein $R^9$ and $R^{11}$ may together form a carbonyl, or $R^{11}$ and $R^{12}$ may together form a carbonyl, or $R^{13}$ and $R^{14}$ may together form a carbonyl, or $R^{15}$ and $R^{16}$ may together form a carbonyl. In yet another embodiment, $R^9$, $R^{10}$, $R^{11}$, $R^{12}$, $R^{13}$, $R^{14}$, $R^{15}$ and $R^{16}$ are each independently selected from the group consisting of hydrogen or $C_{1-2}$ alkyl, wherein $R^9$ and $R^{10}$ may together form a carbonyl, or $R^{11}$ and $R^{12}$ may together form a carbonyl, or $R^{13}$ and $R^{14}$ may together form a carbonyl, or $R^{15}$ and $R^{16}$ may together form a carbonyl. In a more preferred embodiment, $R^9$, $R^{10}$, $R^{11}$, $R^{12}$, $R^{13}$, $R^{14}$, $R^{15}$ and $R^{16}$ are each independently selected from the group consisting of hydrogen, or methyl, wherein $R^9$ and $R^{10}$ may together form a carbonyl, or $R^{11}$ and $R^{12}$ may together form a carbonyl, or $R^{13}$ and $R^{14}$ may together form a carbonyl, or $R^{15}$ and $R^{16}$ may together form a carbonyl. In another embodiment, $R^9$, $R^{10}$, $R^{11}$, $R^{12}$, $R^{13}$, $R^{14}$, $R^{15}$ and $R^{16}$ are each independently selected from the group consisting of hydrogen, or $C_{1-2}$ alkyl, wherein the alkyl substituent is optionally substituted with 1 substituent selected from the group consisting of $N(R^{20})_2$, or aryl or wherein $R^9$ and $R^{10}$ may together form a carbonyl. In another preferred embodiment, $R^9$, $R^{10}$, $R^{11}$, $R^{12}$, $R^{13}$, $R^{14}$, $R^{15}$ and $R^{16}$ are each independently selected from the group consisting of hydrogen or $C_{1-2}$ alkyl, or wherein $R^9$ and $R^{10}$ may together form a carbonyl. In still another preferred embodiment, $R^{11}$ and $R^{15}$ are each selected from the group consisting of hydrogen or methyl, $R^9$, $R^{11}$, $R^{12}$, $R^{13}$, $R^{14}$ and $R^{16}$ are each hydrogen and $R^9$ and $R^{10}$ may together form a carbonyl. In another preferred embodiment, $R^9$, $R^{10}$, $R^{11}$, $R^{12}$, $R^{13}$, $R^{14}$, $R^{15}$ and $R^{16}$ are each hydrogen.

In one preferred embodiment, $R^{17}$ is a heteroaryl that is optionally substituted with from 1 to 2 substituents selected from the group consisting of hydrogen, halo, $CF_3$, $OR^{20}$, $N(R^{20})_2$, $CON(R^{20})_2$, $C_{1-3}$ alkyl, aryl, or heteroaryl, wherein the alkyl and aryl substituents are optionally substituted with 1 substituent independently selected from the group consisting of halo, $CF_3$, $OR^{20}$, or $N(R^{20})_2$. In another embodiment, $R^{17}$ is a heteroaryl that is a fused 6,5 membered ring system containing from 1 to 5 heteroatoms each selected from the group consisting of N, O, or S that is optionally substituted with from 1 to 3 substituents selected from the group consisting of hydrogen, halo, $NO_2$, $CF_3$, CN, $OR^{20}$, $SR^{20}$, $N(R^{20})_2$, $S(O)R^{22}$, $SO_2R^{22}$, $SO_2N(R^{20})_2$, $NR^{20}CO_2R^{22}$, $NR^{20}CON(R^{20})_2$, $COR^{20}$, $CO_2R^{20}$, CON $(R^{20})_2$, $NR^{20}SO_2R^{22}$, $C_{1-15}$ alkyl, $C_{2-15}$ alkenyl, $C_{2-15}$ alkynyl, heteroaryl, aryl, or heteroaryl, wherein the alkyl and aryl substituents are optionally substituted with 1 substituent independently selected from the group consisting of halo, $NO_2$, $CF_3$, CN, $OR^{20}$, $SR^{20}$, $N(R^{20})_2$, $S(O)R^{22}$, or $SO_2R^{22}$. In this embodiment, $R^{17}$ is preferably a heteroaryl that is a fused 6,5 membered ring system containing from 1 to 3 heteroatoms selected from the group consisting of N, O, or S that is optionally substituted with from 1 to 2 substituents selected from the group consisting of hydrogen, halo, $CF_3$, $OR^{20}$, $N(R^{20})_2$, $CON(R^{20})_2$, $C_{1-8}$ alkyl, $C_{2-8}$ alkenyl, $C_{2-8}$ alkynyl, aryl, or heteroaryl, wherein the alkyl and aryl substituents are optionally substituted with 1 substituent independently selected from the group consisting of halo, $CF_3$, $OR^{20}$, or $N(R^{20})_2$. More preferably $R^{17}$ is a heteroaryl that is a fused 6,5 membered ring system containing from 1 to 2 heteroatoms selected from the group consisting of N, O, or S that is optionally substituted with from 1 to 2 substituents selected from the group consisting of hydrogen, halo, $CF_3$, $OR^{20}$, $N(R^{20})_2$, $CON(R^{20})_2$, $C_{1-3}$ alkyl, aryl, or heteroaryl, wherein the alkyl and aryl substituents are optionally substituted with 1 substituent selected from the group consisting of halo, $CF_3$, or $OR^{20}$. Even more preferably in this embodiment, $R^{17}$ is a heteroaryl that is a fused 6,5 membered ring system selected from the group consisting of indole, benzothiazole, and benzoxazole that is optionally substituted with from 1 to 2 substituents selected from the group consisting of hydrogen, halo, $CF_3$, $OR^{20}$, $N(R^{20})_2$, $CON(R^{20})_2$, $C_{1-3}$ alkyl, aryl, or heteroaryl, wherein the alkyl and aryl substituents are optionally substituted with 1 substituent selected from the group consisting of halo, $CF_3$, or $OR^{20}$. In this preferred embodiment, $R^{17}$ is preferably benzothiazole that is optionally substituted with 1 substituent selected from the group consisting of hydrogen, halo, $CF_3$, $OR^{20}$, $N(R^{20})_2$, $CON(R^{20})_2$, $C_{1-3}$ alkyl, or aryl, wherein the alkyl and aryl substituents are optionally substituted with 1 substituent selected from the group consisting of halo or $CF_3$. More preferably $R^{17}$ is benzothiazole that is optionally substituted at the 2-position with 1 substituent selected from the group consisting of hydrogen, methyl or phenyl. In an alternative preferred embodiment, $R^{17}$ is 5-substituted benzothiazole that is optionally substituted with 1 substituent selected from the group consisting of hydrogen, halo, $CF_3$, $OR^{20}$, $N(R^{20})_2$, $CON(R^{20})_2$, $C_{1-3}$ alkyl, or aryl, wherein the alkyl and aryl substituents are optionally substituted with 1 substituent selected from the group consisting of halo or $CF_3$. The 5-substituted benzothiazole is preferably substituted at the 2-position with 1 substituent selected from the group consisting of hydrogen, methyl or phenyl.

In another preferred embodiment, $R^{17}$ is a heteroaryl that is a fused 6, 6 membered ring system containing from 1 to 4 nitrogen atoms that is optionally substituted with from 1 to 3 substituents selected from the group consisting of hydrogen, halo, $NO_2$, $CF_3$, CN, $OR^{20}$, $SR^{20}$, $N(R^{20})_2$, $S(O)R^{22}$, $SO_2R^{22}$, $SO_2N(R^{20})_2$, $NR^{20}CO_2R^{22}$, $NR^{20}CON(R^{20})_2$, $COR^{20}$, $CO_2R^{20}$, $CON(R^{20})_2$, $NR^{20}SO_2R^{22}$, $C_{1-15}$ alkyl, $C_{2-15}$ alkenyl, $C_{2-15}$ alkynyl, heterocyclyl, aryl, or heteroaryl, wherein the alkyl and aryl substituents are optionally substituted with 1 substituent independently selected from the group consisting of halo, $NO_2$, $CF_3$, CN, $OR^{20}$, $SR^{20}$, $N(R^{20})_2$, $S(O)R^{22}$, or $SO_2R^{22}$. More preferably, $R^{17}$ is a heteroaryl that is a fused 6, 6 membered ring system containing from 1 to 3 nitrogen atoms that is optionally substituted with from 1 to 2 substituents selected from the group consisting of hydrogen, halo, $CF_3$, $OR^{20}$, $N(R^{20})_2$, $CON(R^{20})_2$, $C_{1-8}$ alkyl, $C_{2-8}$ alkenyl, $C_{2-8}$ alkynyl, aryl, or heteroaryl, wherein the alkyl and aryl substituents are optionally substituted with 1 substituent independently selected from the group consisting of halo, $CF_3$, $OR^{20}$, or $N(R^{20})_2$. Most preferably, $R^{17}$ is a heteroaryl that is a fused 6, 6 membered ring system containing from 1 to 2 nitrogen atoms that is optionally substituted with methyl;

In yet another preferred embodiment, $R^{17}$ is a 5 or 6-membered ring containing from 1 to 3 heteroatoms selected from the group consisting of N, S, or O that is optionally substituted with from 1 to 3 substituents selected from the group consisting of hydrogen, halo, $NO_2$, $CF_3$, CN, $OR^{20}$, $SR^{20}$, $N(R^{20})_2$, $S(O)R^{22}$, $SO_2R^{22}$, $SO_2N(R^{20})_2$, $NR^{20}CO_2R^{22}$, $NR^{20}CON(R^{20})_2$, $COR^{20}$, $CO_2R^{20}$, $CON(R^{20})_2$, $NR^{20}SO_2R^{22}$, $C_{1-15}$ alkyl, $C_{2-15}$ alkenyl, $C_{2-15}$ alkynyl, heterocyclyl, aryl, or heteroaryl, wherein the alkyl and aryl substituents are optionally substituted with 1 substituent independently selected from the group consisting of halo, $NO_2$, $CF_3$, CN, $OR^{20}$, $SR^{20}$, $N(R^{20})_2$, $S(O)R^{22}$, or $SO_2R^{22}$. More preferably, $R^{17}$ is a 5 or 6 membered ring including from 1 to 3 heteroatoms selected from N, S, or O nitrogen atoms that is optionally substituted with from 1 to 2 substituents selected from the group consisting of hydrogen, halo, $CF_3$, $OR^{20}$, $N(R^{20})_2$, $CON(R^{20})_2$, $C_{1-8}$ alkyl, $C_{2-8}$ alkenyl, $C_{2-8}$ alkynyl, aryl, or heteroaryl, wherein the alkyl and aryl substituents are optionally substituted with 1 substituent independently selected from the group consisting of halo, $CF_3$, $OR^{20}$, or $N(R^{20})_2$. Even more preferably, $R^{17}$ is a 6 membered ring including from 1 to 2 nitrogen atoms that is optionally substituted with from 1 to 2 substituents selected from the group consisting of hydrogen, halo, $CF_3$, $OR^{20}$, $N(R^{20})_2$, $CON(R^{20})_2$, $C_{1-8}$ alkyl, $C_{2-8}$ alkenyl, $C_{2-8}$ alkynyl, aryl, or heteroaryl, wherein the alkyl and aryl substituents are optionally substituted with 1 substituent independently selected from the group consisting of halo, $CF_3$, $OR^{20}$, or $N(R^{20})_2$. Most preferably in this embodiment, $R^{17}$ is a 6 membered ring containing from 1 to 2 nitrogen atoms that is optionally substituted with methyl.

In yet still another preferred embodiment, $R^{17}$ is a heteroaryl that is a fused 6,5 membered ring system selected from the group consisting of benzothiazole, and benzoxazole that is optionally substituted with 1 substituent selected from the group consisting of hydrogen, $CF_3$, $OR^{20}$, $C_{1-3}$ alkyl, or aryl, wherein the alkyl and aryl substituents are optionally substituted with 1 substituent selected from the group consisting of halo or $CF_3$ and preferably optionally substituted with methyl.

In a preferred embodiment, $R^{20}$ is selected from the group consisting of H, $C_{1-15}$ alkyl, aryl, or heteroaryl, wherein the alkyl and aryl substituents are optionally substituted with 1 substituent selected from the group consisting of halo, alkyl, monoalkylamino, dialkylamino, alkylcyano, —O—$C_{1-6}$ alkyl, or $CF_3$. $R^{20}$ is selected from the group consisting of H, $C_{1-5}$ alkyl, aryl, or heteroaryl, wherein the alkyl and aryl substituents are optionally substituted with 1 substituent selected from the group consisting of halo, —OMe, or $CF_3$. In a more preferred embodiment, $R^{20}$ is selected from the group consisting of H, $C_{1-3}$ alkyl, or aryl, wherein the alkyl and aryl substituents are optionally substituted with 1 substituent individually selected from the group consisting of halo, —OMe, and $CF_3$. Most preferably, $R^{20}$ is selected from the group consisting of H or $C_{1-3}$ alkyl and most preferably H or methyl.

In a preferred embodiment, $R^{22}$ is selected from the group consisting of $C_{1-15}$ alkyl, aryl, or heteroaryl wherein the alkyl and aryl substituents are optionally substituted with 1 substituent selected from the group consisting of halo, alkyl, monoalkylamino, dialkylamino, alkyl amide, aryl amide, heteroaryl amide, CN, O—$C_{1-6}$ alkyl, $CF_3$, or heteroaryl.

In a most preferred embodiment, this invention is a substituted piperazine compound selected from the group consisting of N-(2,6-dimethyl-phenyl)-2-(4-{2-hydroxy-3-[2-(3-trifluoromethylphenyl)-benzoxazol-5-yloxy]-propyl}-piperazin-1-yl)acetamide, 2-{4-[3-(benzothiazol-2-yloxy)-2-hydroxy-propyl]-piperazin-1-yl}-N-(2,6-dimethylphenyl) acetamide, N-(2,6-dimethylphenyl)-2-{4-[2-hydroxy-3-(2-methyl-benzothiazol-5-yloxy)-propyl]-piperazin-1-yl}acetamide,4-(3-{4-[(2,6-dimethylphenylcarbamoyl)-methyl]-piperazin-1-yl}-2-hydroxy-propoxy)-1 H-indole-2-carboxylic acid amide, 2-{4-[3-(benzothiazol-6-yloxy)2-hydroxy-propyl]-piperazin-1-yl}-N-(2,6-dimethyl-phenyl)-acetamide, N-(2,6-dimethylphenyl)-2-{4-[2-hydroxy-3-(2-methyl-benzothiazol-6-yloxy)-propyl]-piperazin-1-yl}aceamide, N-(2,6-dimethylphenyl)-2-{4-[2-hydroxy-3-(2-methyl-benzothiazol-5-yloxy)-propyl]-3,5-dimethyl-piperazine-1-yl}acetamide, 2-{4-[2-hydroxy-3-(2-methyl-benzothiazol-5-yloxy)-propyl]-piperazin-1-yl}-N-(4-hydroxy-phenyl)acetamide, N-(2,6-dimethylphenyl)-2-{4-[2-hydroxy-3-(2-phenyl-benzothiazol-5-yloxy)-propyl]-piperazin-1-yl}acetamide, N-(2,6)-dimethylphenyl)-2-{4-[2-hydroxy-3-(2-phenyl-benzoxazol-5-yloxy)-propyl]-piperazin-1-yl}acetamide, N-(2,6-dimethylphenyl)2-{4-[2-hydroxy-3-(2-phenyl-benzothiazol-7-yloxy)-propyl]-piperazin-1-ylacetamide, N-(2,6-dimethylphenyl)-2-{4-[2-hydroxy-3-(2-methyl-benzothiazol-5-yloxy)-propyl]-2-oxo-piperazin-1-yl}acetamide, N-(2,6)-dimethylphenyl)-2-{4-[2-hydroxy-3-(2-methyl-benzoxazol-5-yloxy)-propyl]-piperazin-1-yl}acetamide, N-(2,6-dimethylphenyl)-2-(4-{2-hydroxy-3-[2-(4-trifluoromethyl-phenyl)-benzoxazol-5-yloxy]-propyl}-piperazin-1-yl)acetamide, N-(2,6-dimethylphenyl)-2-(4-[2-hydroxy-3-(quinoxalin-2-yloxy)-propyl]-piperazin-1-yl}acetamide, N-(2,6)-dimethylphenyl)-2-{4-[2-hydroxy-3-(pyridin-3-yloxy)-propyl]-piperazin-1)-yl}acetamide, N-(2,6-dimethylphenyl)-2-{4-[2-hydroxy-3-(quinolin-4-yloxy)-propyl]-piperazin-1-yl}acetamide, N-(2,6-dimethylphenyl)-2-{4-[2-hydroxy-3-(isoquinolin-5-yloxy)-propyl]-piperazin-1-yl}acetamide, N-(2,6-dimethylphenyl)-2-{4-[2-hydroxy-3-(quinolin-6-yloxy)-propyl]-piperazin-1-yl}acetamide, N-(2,6-dimethylphenyl)-2-{4-[2-hydroxy-3-(2-methyl-quinolin-7-yloxy)-propyl]-piperazin-1-yl}acetamide, 2-{4-[3-(benzothiazol-2-ylamino)-2-hydroxypropyl]piperazinyl}-N-(2,6-dimethylphenyl) acetamide, 2-{4-[3-(benzoxazol-2-ylamino)-2-hydroxypropyl]piperazinyl}-N-(2,6-dimethylphenyl) acetamide and mixtures thereof.

The following definitions apply to terms as used herein.

"Halo" or "Halogen"—alone or in combination means all halogens, that is, chloro (Cl), fluoro (F), bromo (Br), iodo (I).

"Hydroxyl" refers to the group —OH.

"Thiol" or "mercapto" refers to the group —SH.

"Alkyl"—alone or in combination means an alkane-derived radical containing from 1 to 20, preferably 1 to 15, carbon atoms (unless specifically defined). It is a straight chain alkyl, branched alkyl or cycloalkyl. Preferably, straight or branched alkyl groups containing from 1–15, more preferably 1 to 8, even more preferably 1–6, yet more preferably 1–4 and most preferably 1–2, carbon atoms, such as methyl, ethyl, propyl, isopropyl, butyl, t-butyl and the like. The term "lower alkyl" is used herein to describe the straight chain alkyl groups described immediately above. Preferably, cycloalkyl groups are monocyclic, bicyclic or tricyclic ring systems of 3–8, more preferably 3–6, ring members per ring, such as cyclopropyl, cyclobutyl, cyclopentyl, cyclohexyl, adamantyl and the like. Alkyl also includes a straight chain or branched alkyl group that contains or is interrupted by a cycloalkyl portion. The straight chain or branched alkyl group is attached at any available point to produce a stable compound. Examples of this include, but are not limited to, 4-(isopropyl)-cyclohexylethyl or 2-methyl-cyclopropylpentyl. A substituted alkyl is a straight chain alkyl, branched alkyl, or cycloalkyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Alkenyl"—alone or in combination means a straight, branched, or cyclic hydrocarbon containing 2–20, preferably 2–17, more preferably 2–10, even more preferably 2–8, most preferably 2 to 4 carbon atoms with at least one, preferably 1–3, more preferably 1–2, and most preferably one, carbon to carbon double bond. In the case of a cycloalkyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, isopropenyl, butenyl, cyclohexenyl, cyclohexenylalkyl and the like. A substituted alkenyl is the straight chain alkenyl, branched alkenyl or cycloalkenyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxy, alkoxycarbonyl, aryloxycarbonyl, heteroaryloxycarbonyl, or the like attached at any available point to produce a stable compound.

"Alkynyl"—alone or in combination means a straight or branched hydrocarbon containing 2–20, preferably 2–17, more preferably 2–10, even more preferably 2–8, most preferably 2–4, carbon atoms containing at least one, preferably one, carbon to carbon triple bond. Examples of alkynyl groups include ethynyl, propynyl, butynyl and the like. A substituted alkynyl refers to the straight chain alkynyl or branched alkynyl defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like attached at any available point to produce a stable compound.

"Alkyl alkenyl" refers to a group —R—CR'=CR'''R"", where R is lower alkyl, or substituted lower alkyl, R', R''', R"" may independently be hydrogen, halogen, lower alkyl, substituted lower alkyl, acyl, aryl, substituted aryl, hetaryl, or substituted hetaryl as defined below.

"Alkyl alkynyl" refers to a groups —RC≡CR' where R is lower alkyl or substituted lower alkyl, R' is hydrogen, lower alkyl, substituted lower alkyl, acyl, aryl, substituted aryl, hetaryl, or substituted hetaryl as defined below.

"Alkoxy" denotes the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

"Alkylthio" denotes the group —SR, —S(O)$_{n=1-2}$—R, where R is lower alkyl, substituted lower alkyl, aryl, substituted aryl, aralkyl or substituted aralkyl as defined herein.

"Acyl" denotes groups —C(O)R, where R is hydrogen, lower alkyl substituted lower alkyl, aryl, substituted aryl and the like as defined herein.

"Aryloxy" denotes groups —OAr, where Ar is an aryl, substituted aryl, heteroaryl, or substituted heteroaryl group as defined herein.

"Amino" denotes the group NRR', where R and R' may independently by hydrogen, lower alkyl, substituted lower alkyl, aryl, substituted aryl, hetaryl, or substituted hetaryl as defined herein or acyl.

"Amido" denotes the group —C(O)NRR', where R and R' may independently by hydrogen, lower alkyl, substituted lower alkyl, aryl, substituted aryl, hetaryl, substituted hetaryl as defined herein.

"Carboxyl" denotes the group —C(O)OR, where R is hydrogen, lower alkyl, substituted lower alkyl, aryl, substituted aryl, hetaryl, and substituted hetaryl as defined herein.

"Aryl"—alone or in combination means phenyl or naphthyl optionally carbocyclic fused with a cycloalkyl of preferably 5–7, more preferably 5–6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Substituted aryl" refers to aryl optionally substituted with one or more functional groups, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroaryl"—alone or in combination means a monocyclic aromatic ring structure containing 5 or 6 ring atoms, or a bicyclic aromatic group having 8 to 10 atoms, containing one or more, preferably 1–4, more preferably 1–3, even more preferably 1–2, heteroatoms independently selected from the group O, S, and N, and optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-disubstituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinazolinyl, purinyl, quinolinyl, isoquinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl, benzothiazolyl, benzoxazolyl, and the like. A substituted heteroaryl contains a substituent attached at an available carbon or nitrogen to produce a stable compound.

"Heterocyclyl"—alone or in combination means a non-aromatic cycloalkyl group having from 5 to 10 atoms in which from 1 to 3 carbon atoms in the ring are replaced by heteroatoms of O, S or N, and are optionally benzo fused or fused heteroaryl of 5–6 ring members and/or are optionally substituted as in the case of cycloalkyl. Heterocycyl is also intended to include oxidized S or N, such as sulfinyl, sulfonyl and N-oxide of a tertiary ring nitrogen. The point of attachment is at a carbon or nitrogen atom. Examples of heterocyclyl groups are tetrahydrofuranyl, dihydropyridinyl, piperidinyl, pyrrolidinyl, piperazinyl, dihydrobenzofuryl, dihydroindolyl, and the like. A substituted hetercyclyl contains a substituent nitrogen attached at an available carbon or nitrogen to produce a stable compound.

"Substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Aralkyl" refers to the group —R—Ar where Ar is an aryl group and R is lower alkyl or substituted lower alkyl group. Aryl groups can optionally be unsubstituted or substituted with, e.g., halogen, lower alkyl, alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Heteroalkyl" refers to the group —R-Het where Het is a heterocycle group and R is a lower alkyl group. Heteroalkyl groups can optionally be unsubstituted or substituted with e.g., halogen, lower alkyl, lower alkoxy, alkylthio, acetylene, amino, amido, carboxyl, aryl, aryloxy, heterocycle, substituted heterocycle, hetaryl, substituted hetaryl, nitro, cyano, thiol, sulfamido and the like.

"Heteroarylalkyl" refers to the group —R-HetAr where HetAr is an heteroaryl group and R lower alkyl or substituted lower alkyl. Heteroarylalkyl groups can optionally be unsubstituted or substituted with, e.g., halogen, lower alkyl, substituted lower alkyl, alkoxy, alkylthio, acetylene, aryl, aryloxy, heterocycle, substituted heterocycle, hetaryl, substituted hetaryl,.nitro, cyano, thiol, sulfamido and the like.

"Cycloalkyl" refers to a divalent cyclic or polycyclic alkyl group containing 3 to 15 carbon atoms.

"Substituted cycloalkyl" refers to a cycloalkyl group comprising one or more substituents with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloheteroalkyl" refers to a cycloalkyl group wherein one or more of the ring carbon atoms is replaced with a heteroatom (e.g., N, O, S or P).

"Substituted cycloheteroalkyl" refers to a cycloheteroalkyl group as herein defined which contains one or more substituents, such as halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloalkyl" denotes the group —R-cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloheteroalkyl" denotes the group —R-cycloheteroalkyl where R is a lower alkyl or substituted lower alkyl. Cycloheteroalkyl groups can optionally be unsubstituted or substituted with e.g. halogen, lower alkyl, lower alkoxy, alkylthio, amino, amido, carboxyl, acetylene, hydroxyl, aryl, aryloxy, heterocycle, substituted heterocycle, hetaryl, substituted hetaryl, nitro, cyano, thiol, sulfamido and the like.

"Optional" and "optionally" mean that the subsequently described event or circumstance may or may not occur, and that the description includes instances where the event or circumstance occurs and instances in which it does not. For example, "optional pharmaceutical excipients" indicates that a formulation so described may or may not include pharmaceutical excipients other than those specifically stated to be present, and that the formulation so described includes instances in which the optional excipients are present and instances in which they are not.

"Treating" and "treatment" refer to any treatment of a disease in a mammal, particularly a human, and include:
(i) preventing the disease from occurring in a subject which may be predisposed to the disease but has not yet been diagnosed as having it;
(ii) inhibiting the disease, i.e., arresting its development; or
(iii) relieving the disease, i.e., causing regression of the disease.

All of the aforementioned embodiments include the pharmaceutically acceptable acid addition salts thereof, particularly the mono- and dihydrochlorides, and mixtures thereof.

The compounds having the general formula Ia (q=O) or Ic (q=S) can be prepared as outlined in Schemes 1–5. A general synthesis of the compounds of this invention is outlined in Scheme 1. Compound IV can be prepared by N-acylation of substituted aniline II with 2-substituted chloroacetylchloride III. Compound II is available commercially or readily prepared through reduction of the corresponding nitrobenzene derivative (acid/SnCl$_2$ or catalytic hydrogenation, see Advanced Organic Chemistry, Ed. J. March, (1992) A. Wiley-Interscience). Some examples of commercially available substituted anilines corresponding to general structure II include 2,6-dimethylaniline, 2,3-dimethylaniline, 2-methylaniline, 4-methylaniline, 4-methylaniline, 2,4-dichloroaniline, 3,4-dichloroaniline, 2,5-dichloroaniline, 2,4-dichloroaniline, 2-chloroaniline, 3-chloroaniline, 2,6-difluoroaniline, 2,5-difluoroaniline, 3,4-difluoroaniline, 2-fluoroaniline, 4-fluoroaniline, 3-fluoroaniline, 2-fluoro-6-chloroaniline, 4-fluoro-3-chloroaniline, 4-acetoxyaniline.

eral structure V include 2-methylpiperazine, 2,5-dimethylpiprazine, 2,6-dimethylpiperazine, 2,3,5,6-tetramethylpiperazine, piperazine-2-carboxylic acid, perhydroquinoxaline, 2-aminomethyl-6-methylpiperazine, 2-aminomethylpiperazine, 2-(o-chlorophenyl)piperazine, and 2-(m-chlorophenyl)piperazine. Deprotection of compound VI can be accomplished using the standard conditions (e.g. for Boc group use TFA, for CBZ and benzyl use hydrogenation). Compound Ia or Ic can be prepared by reacting compound VII with epoxide VIII through warming in an appropriate solvent (ethanol, DMF, CHCl$_2$, THF) or by stirring at room temperature in the presence of a lanthamide (III) Lewis acid (Chini, M et al., *Tetrahedron Lett.*, 35: 433–36 (1994).

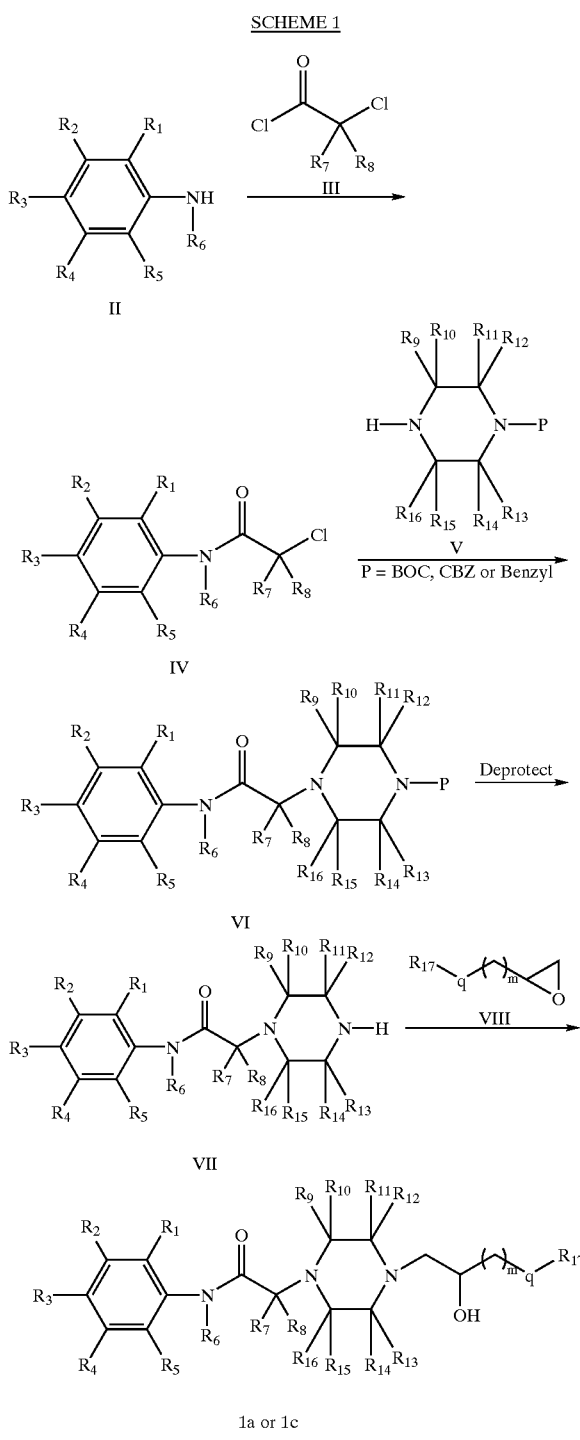

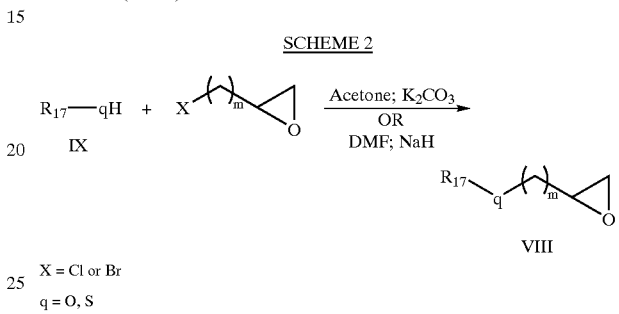

Epoxide VIII (where m=1, 2, or 3) can be prepared as outlined in Scheme 2. Heating substituted phenol, or thiophenol IX with epichlorohydrin, epibromohydrin, or 4-bromo-1,2-epoxybutane and potassium carbonate in acetone or sodium hydride in DMF can afford epoxide VIII. Compound IX can be obtained from commercial resources. Examples of commercially available compounds corresponding to structure XI include 2-methyl-5-hydroxybenzothiazole, 2-hydroxybenzothiazole, 8-hydroxyquinolidine, 6-hydroxyquinoline, 4-hydroxyquinoline, 5-hydroxyisoquinoline, 3-hydroxypyridine, 2-quinoxalinol, and 4-(imidazol-1-yl)phenol. In some cases compound VIII can be obtained from commercial sources. Examples of commercially available compounds corresponding to general structure VIII include 4-glycidyloxy-2-indolecarboxamide.

Compound IX can in turn be prepared by the deprotection of the corresponding methyl or benzyl ethers (X) using Lewis acids as shown in Scheme 3 (BBr$_3$, BF$_3$, etc.—see Advanced Organic Chemistry, Ed. J. March (1992) A. Wiley Intersciences, p 434). Benzyl ethers can also be deprotected by refluxing with palladium hydroxide in ethanol/cyclohexene (see Catalytic hydrogenation over platinum metals, P. N. Rylander, Academic Press, New York, N.Y., (1976) p 464). Commercially available methyl ethers include 6-methoxy-2-methyl-benzothiazole.

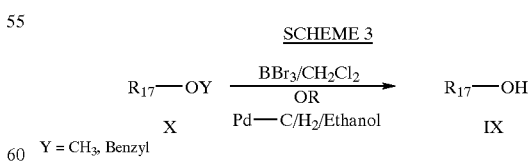

Compound VI can be obtained by reacting compound IV with N-protected substituted piperazine V through warming in an appropriate solvent (e.g. DMF, EtOH). Protection of the nitrogen of compound V is only required when it is useful to control the regiochemistry of the addition of Compound V with compound IV. In some cases, compound V can be obtained from commercial resources. Examples of commercially available compounds corresponding to gen- Compound IX can also be prepared by the diazotization of the corresponding amino compounds (XI) as shown in Scheme 4 (Boggust, W. A and Cocker, W. J. Chem. Soc. 1949, 355). Commercially available amines include 6-amino-benzothiazole.

SCHEME 4

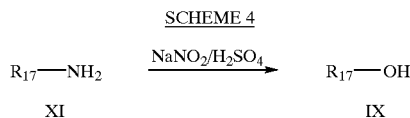

The 6, 5 fused ring system of compound X can be prepared by the cyclization of commercially available ethers of 2-aminophenols, 2-aminothiophenols, or 2-aminoanilines (XII) with orthoesters (XIII) (Musser, J. H. et al., J. Med. Chem. 1985, 28, 1255–1259) or imidates (XIV) (Gregory, G. I. Et al., J. Chem. Soc. Perkin Trans. 1, 1973, 47–51) as shown in Scheme 5 and 6 respectively. Commercially available, ethers of aminophenols include 4-methoxy-2-aminophenol, orthoesters include trimethyl orthoformate and trimethyl orthoacetate, imidates include ethyl acetimidate hydrochloride, and ethyl benzimidate hydrochloride.

SCHEME 5

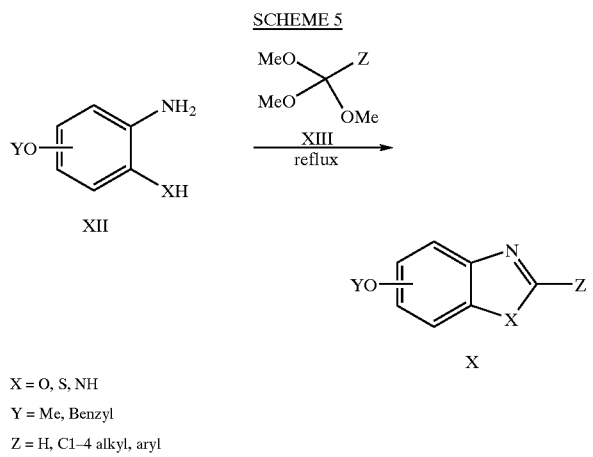

X = O, S, NH
Y = Me, Benzyl
Z = H, C1–4 alkyl, aryl

SCHEME 6

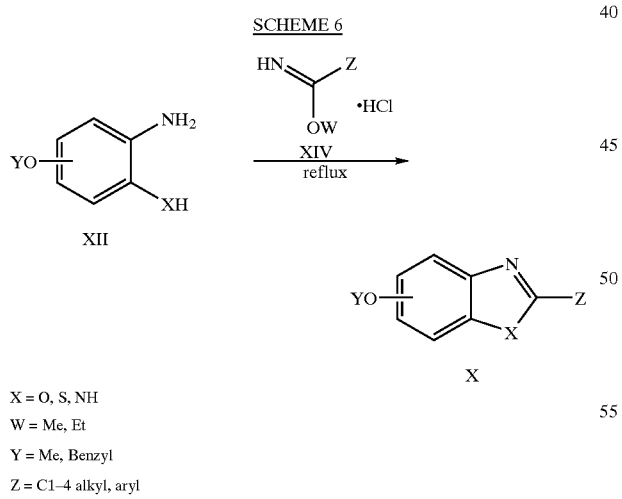

X = O, S, NH
W = Me, Et
Y = Me, Benzyl
Z = C1–4 alkyl, aryl

The thiophenol analog of compound XII can be prepared from the commercially available compound XV by reacting with sodium disulfide hydrate followed by reduction using tin and hydrochloric acid (Dannley, R. L. and Zazaris, D. A; Can. J. Chem. 1965, 43, 2610–2612) as shown in Scheme 7. Commercially available nitro compounds include 3-nitro-4-chloroanisole.

SCHEME 7

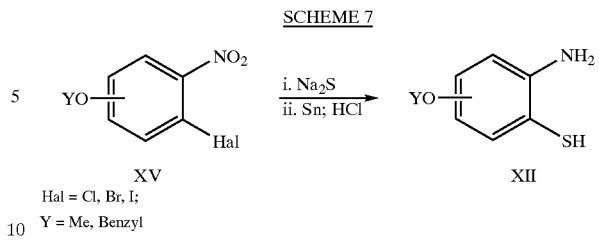

Hal = Cl, Br, I;
Y = Me, Benzyl

Imidate XIV can be prepared by bubbling HCl gas through an alcoholic solution of the commercially available nitrites XVI as shown in Scheme 8. Commercially available nitriles include, benzonitrile, 4-trifluoromethylbenzonitrile and 3-trifluoromethylbenzonitrile.

SCHEME 8

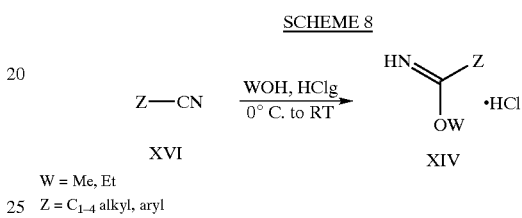

W = Me, Et
Z = $C_{1-4}$ alkyl, aryl

Sulfur containing 6,5 fused ring system of compound X can also be prepared from the commercially available ethers of anilines XVII (Stevens, M. F. G. et al, J. Med. Chem. 1994, 37, 1689–1695) as shown in Scheme 9. Thioamide XX can be obtained by the reaction of Lawesson's reagent with amide XIX which in turn can be prepared by the reaction of compound XVII with compound XVIII. Cyclization of XX with potassium ferrocyanide under basic conditions can afford compound XXI. Commercially available ethers of anilines include benzyloxyanilines and anisidines.

SCHEME 9

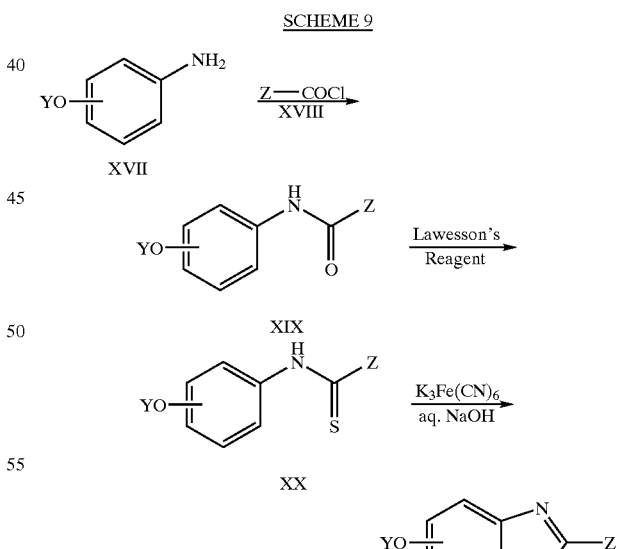

Y = Me, Benzyl
Z = $C_{1-4}$alkyl, aryl

A general synthesis of the compound XXV of this invention is outlined in Scheme 10. Compound XXIV can be prepared by the deprotection of compound XXIII using the standard conditions (e.g. for BOC group use TFA, for CBZ and benzyl use hydrogenation). Compound XXIII in turn can be prepared by the reaction of the commercially available protected monoketopiperazine analog compound XXII with compound IV and sodium hydride in an appropriate solvent (DMF, THF). An example of the commercially available monoketopiperazines include 4-benzyloxycarbonylpiperazine-2-one.

SCHEME 10

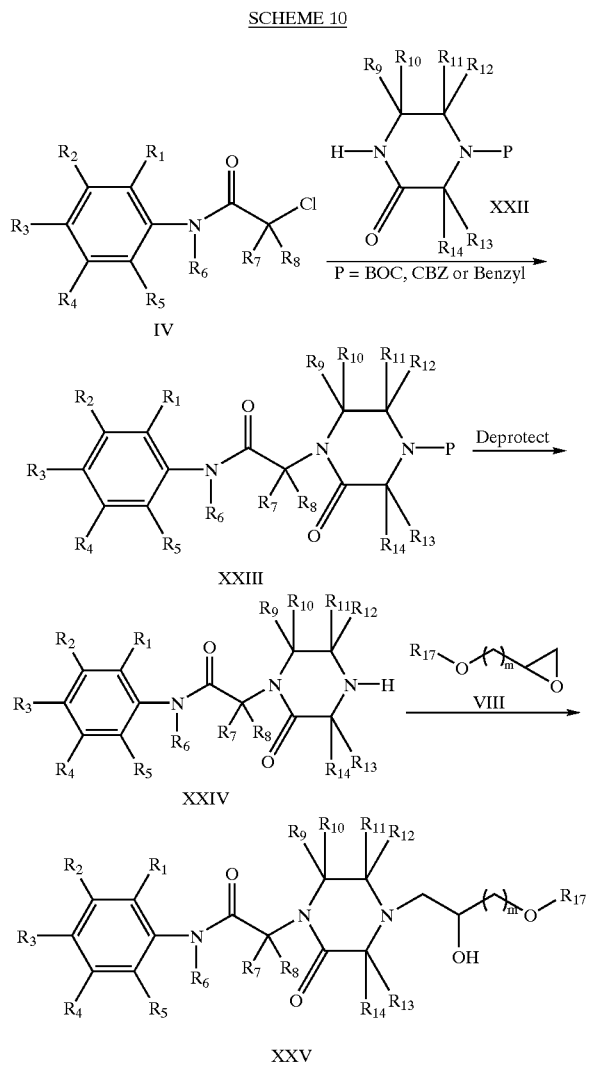

SCHEME 11

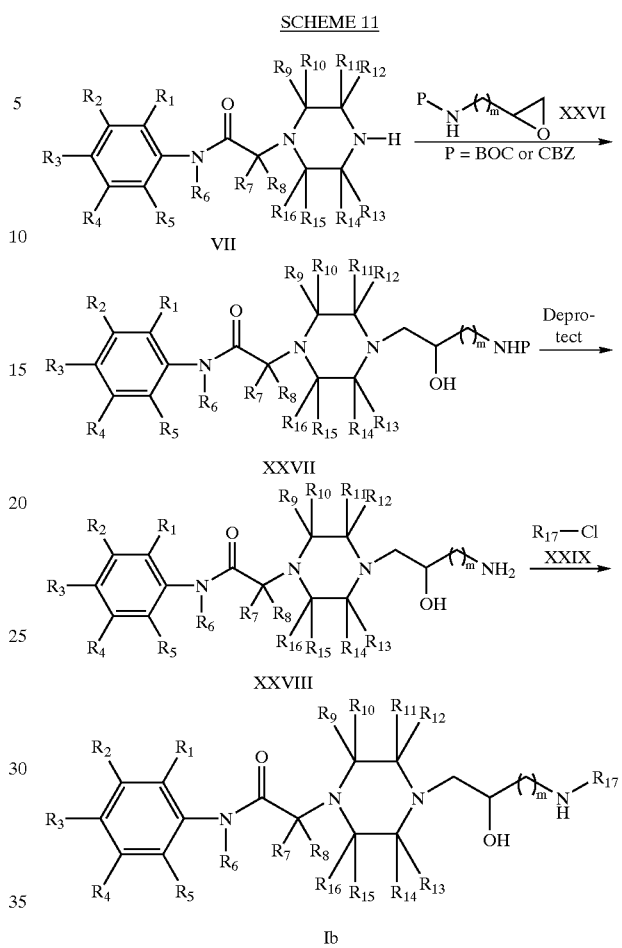

A general synthesis of the compound Ib (q=NH) of this invention is outlined in Schemes 11 and 12. Compound XXVII can be prepared by refluxing compound VII with the epoxide XXVI in a suitable solvent (ethanol, THF). Deprotection of compound XXVII can be accomplished by using standard conditions (e.g. for BOC group use TFA; for CBZ use hydrogenation or Pd(OH)$_2$). Compound Ib can be prepared by refluxing compound XXVIII with compound XXIX in a suitable solvent (ethanol, THF). Commercially available compound XXIX includes 2-chlorobenzothiazole, 2-chlorobenzoxazole, 2-chloropyridine, 2-chloropyrimidine, 2-chloro-4-(trifluoromethyl)pyrimidine, and chloropyrazine.

Epoxide XXVI in turn can be prepared as shown in Scheme 12. Commercially available compound XXX can be protected using the standard conditions (for BOC protection use BOC anhydride; for CBZ protection use CBZ-Cl). Compound XXV can be prepared by the reaction of compound XXXI using m-chloroperbenzoic acid in a suitable solvent (e.g. dichloromethane). An example of a commercially available compound XXX includes by is not limited to allylamine.

SCHEME 12

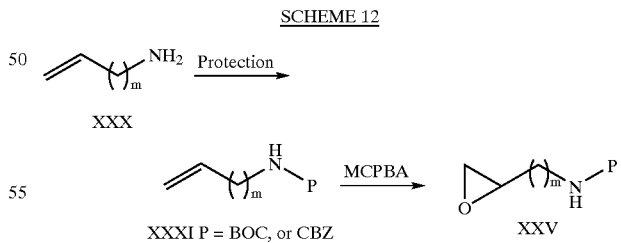

Compound V can be prepared as described in Scheme 13. Alkylation of compound XXXII with alkyl halides using t-BuLi as base can afford compound XXXIII as described by Pohlman et. al. (J. Org. Chem, 1997, 62, 1016–1022). Reduction of XXXIV using diborane can afford the N-benzyl protected version of compound V after N-Boc deprotection with trifluoroacetic acid (TFA) [for the diborane reduction see Jacobson et. al, J. Med. Chem, 1999, 42, 1123–1144].

SCHEME 13

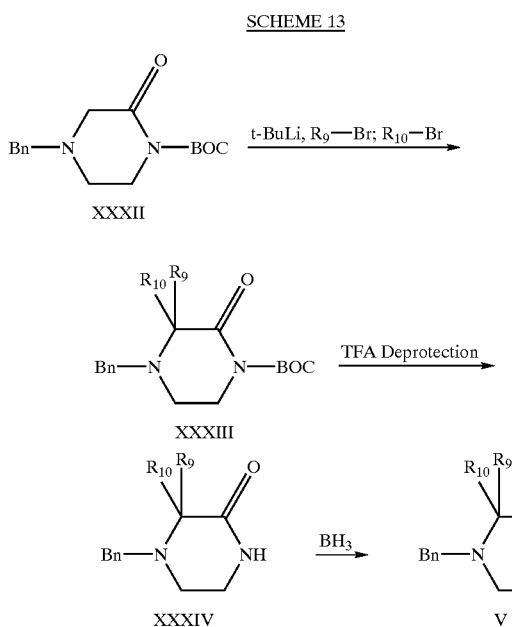

Compound V can also be prepared through standard coupling (eg. EDC or PyBroP) of D or L amino acids and standard deprotection as outlined in Scheme 14 (Cledera, P. et al. Tetrahedron, 1998 p. 12349–12360; Smith, R. A. et al Bioorg. Med. Chem. Lett. 1998, p. 2369–2374). Reduction of the diketopiperazine XXXVII with diborane can afford the N-benzyl protected version of compound V.

SCHEME 14

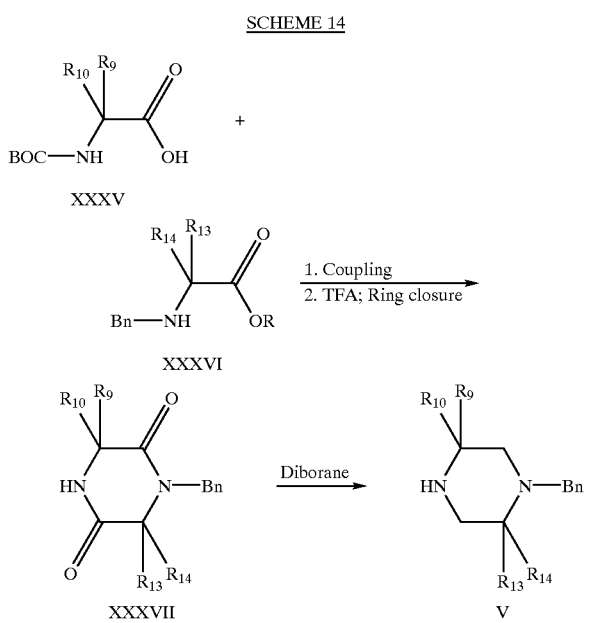

Compound V can also be prepared as described in Scheme 15. Bromination of aldehydes XXXVIII followed by the reaction with ethylene diamine can afford the imine XLI. Catalytic hydrogenation of compound XLI can afford compound V (Bogeso, K. P., et al, J. Med. Chem. 1995, 38, p 4380–4392). Commercially available aldehydes include isobutyraldehyde.

SCHEME 15

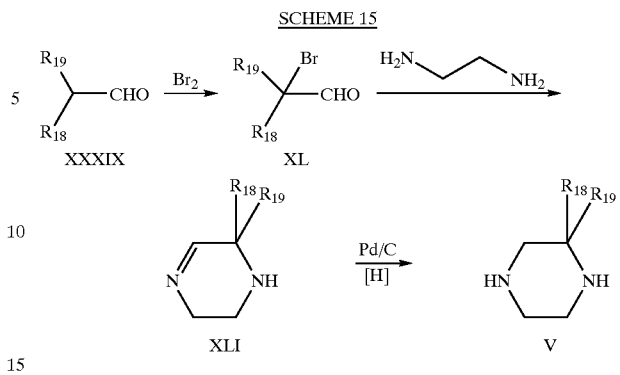

Compound V also includes the bicyclic homologs of piperazine (1S,4S)-(+)-2,5-diazabicyclo[2.2.1]heptane 83, 3,8-diazabicyclo[3.2.1] octane 84, and 2,5-diazabicyclo [2.2.2] octane 85.

83

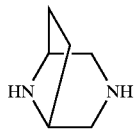

84

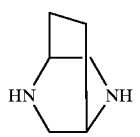

85

Commercially available bicyclic analogs include (1S,4S)-(+)-2,5-diazabicyclo[2.2.1]heptane 83. Compounds 84, 85, and the (1R,4R) isomer of 83 can be prepared by published procedures (for 84 and 85- see Sturm, P. A. et al, J. Med. Chem. 1974, 17, 481–487; for 83 see—Barish, T. F. and Fox, D. E. J. Org. Chem., 1990, 55, 1684–1687).

Specific examples of the preparation of compounds corresponding to the general schemes described above are disclosed in Scheme 16–29 of the Examples which further illustrate alternative methods for preparing compounds of this invention. In particular, 2,6-methylaniline was acylated with 2-chloroacetyl chloride 2 using saturated bicarbonate and ether (1:1) as base and co-solvent, respectively to afford the chloroacetamide derivative 3. Further reaction of compound 3 with piperazine afforded compound 5 through warming in ethanol. Reaction of compound 5 with epoxide 6 by warming both components in ethanol at reflux afforded piperazine derivative 7 as illustrated in Scheme 16. Compound 6 was prepared by warming epichlorohydrin with the phenol 8 in acetone in the presence of $K_2CO_3$ as described in Scheme 17.

SCHEME 16

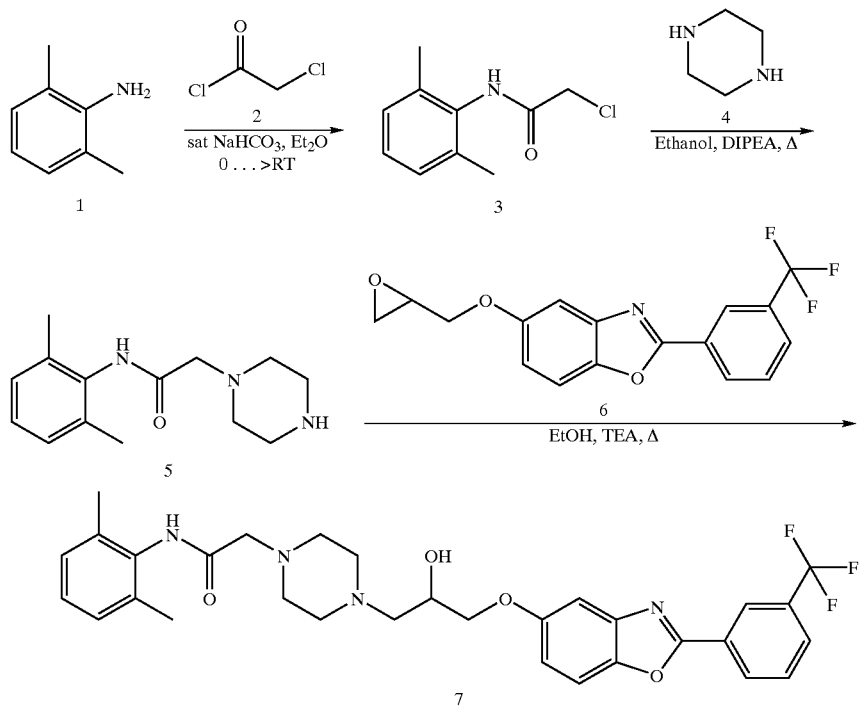

SCHEME 17

SCHEME 18

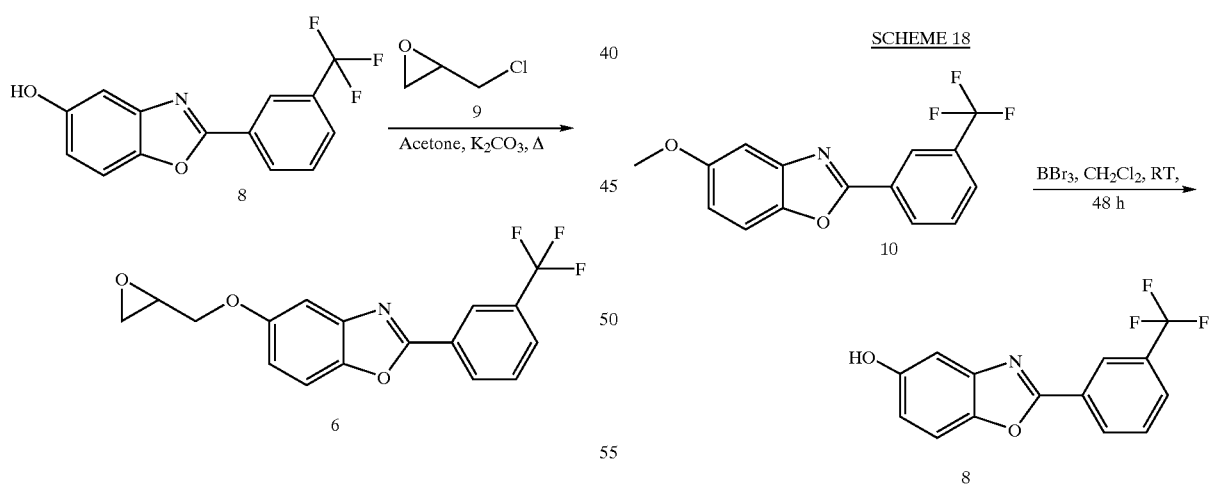

The benzoxazole derivative 8 was prepared by the deprotection of compound 13 as shown in Scheme 18. Compound 10 was prepared by condensation of 2-amino-4-methoxyphenol 12. Compound 12 was obtained by the catalytic hydrogenation of the commercially available 4-methoxy-2-nitrophenol 11, and the benzimidate derivative 13 as shown in Scheme 19. Compound 13 was obtained from 3-trifluoromethylbenzonitrile 14 using a Pinner reaction (ethanoluanhydrous HCl).

SCHEME 19

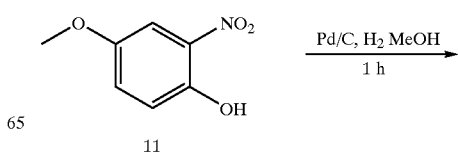

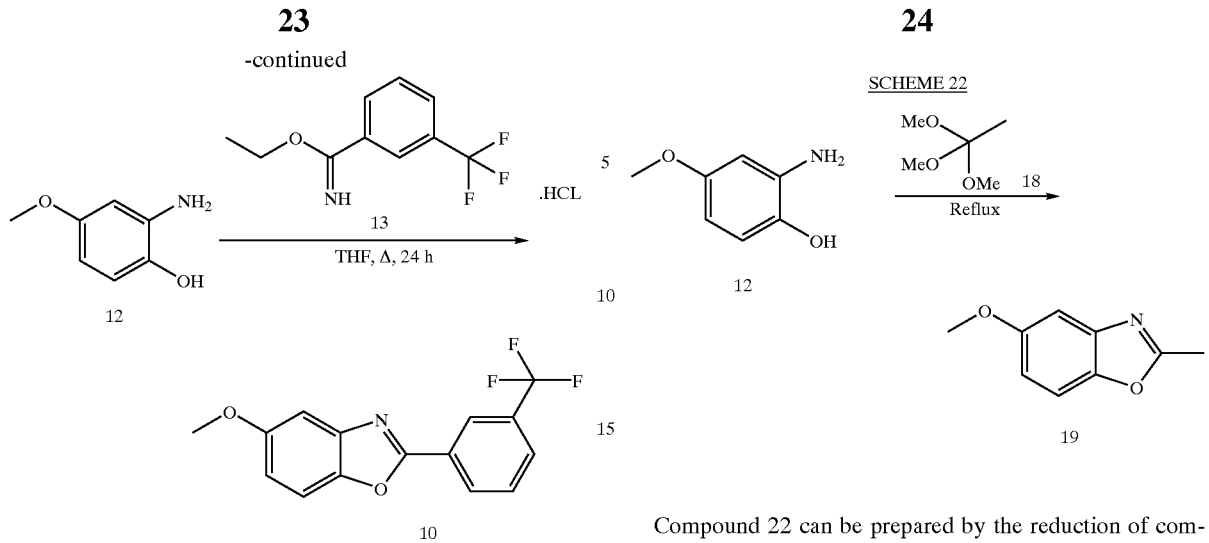

SCHEME 20

Synthesis of the key intermediates that were used in the preparation of the compounds described in this invention are shown in Scheme 21–25. Compound 16 was prepared by the diazotization of the commercially available 6-aminobenzothiazole as shown in scheme 21.

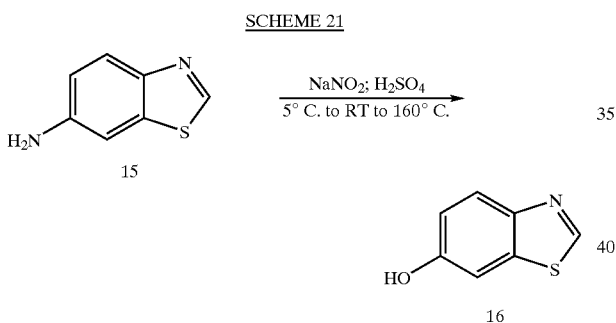

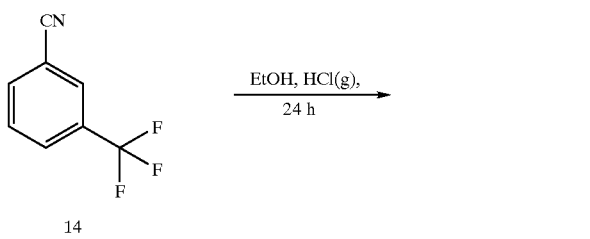

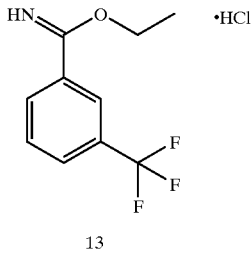

Compound 19 was prepared by condensation of compound 12 with trimethyl orthoacetate 18 as shown in Scheme 22.

Compound 22 can be prepared by the reduction of compound 21 with tin and hydrochloric acid as shown in Scheme 23. Compound 21 was synthesized by reacting compound 20 with sodium disulfide hydrate.

Compound 26 was prepared by the reaction of compound 25 with Lawesson's reagent as shown in Scheme 24. Compound 25 was prepared by the reaction of the aniline 23 with benzoyl chloride 24. Cyclization of the thioamide 26 with potassium ferrocyanide in aqueous sodium hydroxide gave a mixture of compounds 27 and 28. Compounds 27 and 28 were separated by column chromatography.

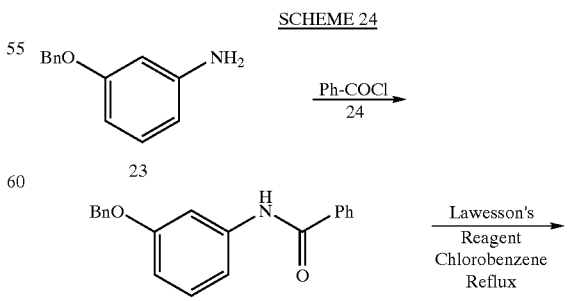

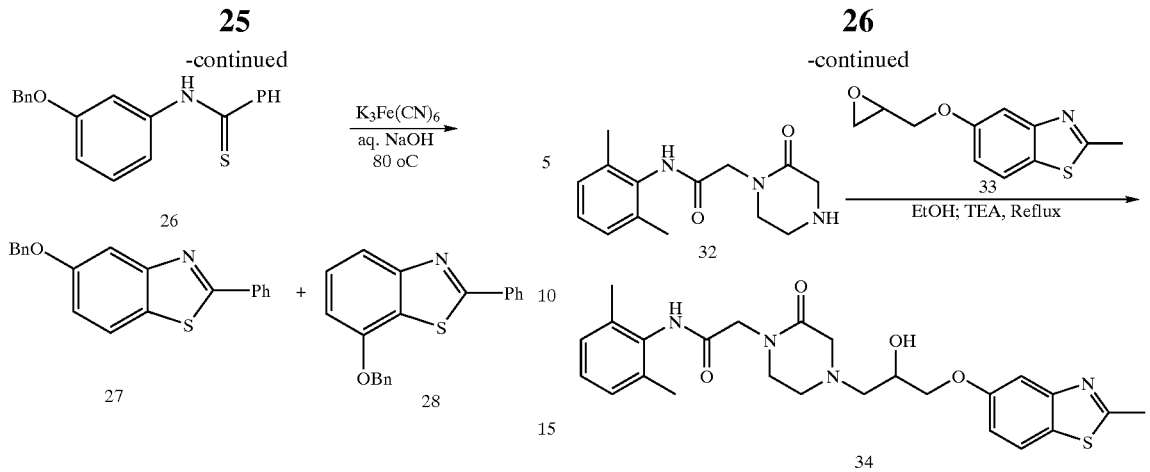

Debenzylation of compound 27 was carried out as shown in Scheme 25 by transfer hydrogenolysis using Pearlmann's catalyst in ethanol/cyclohexene.

SCHEME 25

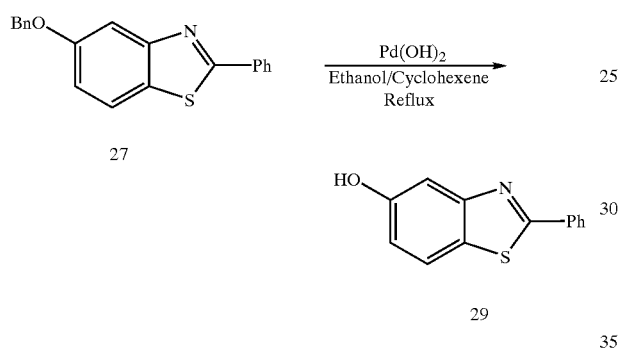

Synthesis of compound 34 of this invention is described in Scheme 26. The amide 3 was prepared as described in Scheme 16. Reaction of 3 with the manion of the anion of the monoketopiperazine 30 formed through treatment with sodium hydride in DMF gave compound 31. Compound 34 was obtained through warming compound 32 with the epoxide 33 in ethanol. Compound 32 was prepared by the deprotection of compound 31 by catalytic dehydrogenation. Epoxide 33 was prepared in the same manner as compound 6 described in Scheme 17.

SCHEME 26

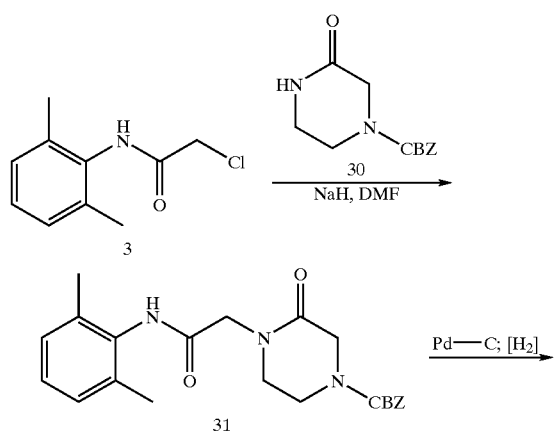

Synthesis of a specific compound 39 of this invention is described in Scheme 27. The synthesis of compound 5 was described previously (Scheme 16). Warming compound 5 to reflux with the epoxide 35 in ethanol gave compound 36. Deprotection of 36 by treatment with palladium hydroxide in ethanol/cyclohexene under reflux conditions gave the amine 37. The final compound 39 was prepared by reacting 37 with 2-chlorobenzothiazole in ethanol and triethylamine.

SCHEME 27

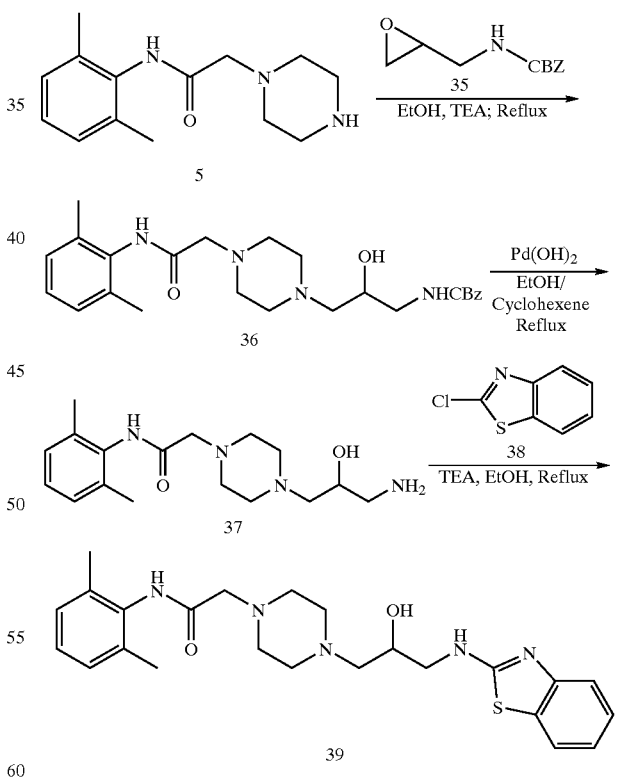

Epoxide 35 was synthesized as described in Scheme 28. Allylamine 40 was reacted with benzyl chloroformate in dichloromethane to afford compound 42. Reaction of m-chloroperbenzoic acid with 42 gave the epoxide 35.

SCHEME 28

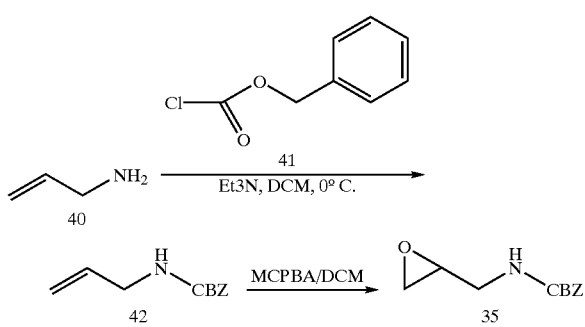

The acid addition salts of the compounds of this invention may be converted to the corresponding free base by treating with a suitable base, such as potassium carbonate or sodium hydroxide, typically in the presence of aqueous solvent, and at a temperature of between about 0 degrees C. and 100 degrees C. The free base form is isolated by conventional means, such as extraction with an organic solvent.

Salts of the compounds of this invention may be interchanged by taking advantage of differential solubilities and volatilities, or by treating with the appropriately loaded ion exchange resin. This conversion is carried out at a temperature between about 0° C. and the boiling point of the solvent being used as the medium for the procedure. Administration of the active compounds and salts described herein can be via any of the accepted modes of administration for therapeutic agents. These methods include oral, parenteral, transdermal, subcutaneous and other systemic modes. The preferred method of administration is oral, except in those cases where the subject is unable to ingest, by himself, any medication. In those instances it may be necessary to administer the composition parentarally.

Depending on the intended mode, the compositions may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions may include one or more conventional pharmaceutical excipients and at least one active compound of this invention or the pharmaceutically acceptable salts thereof and, in addition, may include other medicinal agents, pharmaceutical agents, carriers, adjuvants, diluents, etc.

The amount of active compound administered will, of course, be dependent on the subject being treated, the subject's weight, the severity of the affliction, the manner of administration and the judgment of the prescribing physician. However, an effective dosage is in the range of 0.1–30 mg/kg/day, preferably 0.5–20 mg/kg/day. For an average 70 kg human, this would amount to 7–2100 mg per day, or preferably 35–1400 mg/day. Since many of the effects of the compounds herein (protect skeletal muscles against damage resulting from trauma; protect skeletal muscles subsequent to muscle or systemic diseases such as intermittent claudication; treat shock conditions; preserve donor tissue and organs used in transplants; and treat cardiovascular diseases including atrial and ventricular arrhythmias, Prinzmetal's (variant) angina, stable angina, exercise induced angina, congestive heart disease, and myocardial infarction) are achieved through a similar mechanism (partial fatty acid oxidation inhibition) dosages (and forms of administration) are all generally within the same general and preferred ranges for all these utilities.

For solid compositions, conventional non-toxic solid include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administrable compositions can, for example, be prepared by dissolving, dispersing, etc. an active compound as defined above and optional pharmaceutical adjuvants in a excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound(s), a therapeutically effective amount, i.e. in an amount effective to alleviate the symptoms of the subject being treated. For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%–95% active ingredient, preferably 1–70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795, which is incorporated herein by reference. In another recent approach, the compositions of this invention can be administered orally in a sustained release dosage form using the compositions and/or methods disclosed in U.S. patent application Ser. No. 09/321,522, filed on May 27, 1999, the specification of which is incorporated herein by reference.

It is within the scope of this invention to administer one or more compounds of this invention to a mammal, and preferably to a human by other known routes of pharmaceutical dosage form administration including, but not limited to by bolus, intravenously, transdermally, through inhalation, sub-cutaneously, or any other therapeutic agent administration method or route know to one skilled in the art.

EXAMPLE 1

N-(2,6-Dimethyl-phenyl)-2-(4-{2-hydroxy-3-[2-(3-trifluoromethylphenyl)benzoxazol-5-yloxyl-propyl}-piperazin-1-yl)acetamide (7)

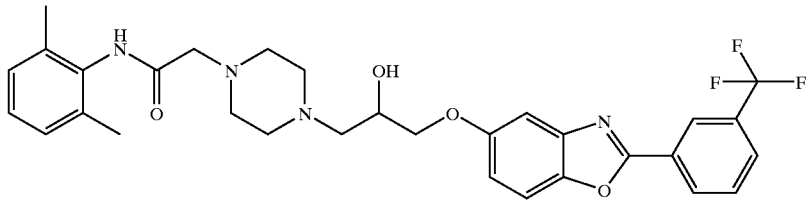

Part A.
Synthesis of N-(2,6-Dimethylphenyl)-2-chloroacetamide (3):

2,6-dimethylaniline (9.8 g, 81.2 mmol) was dissolved in ether (100 mL) and saturated aqueous NaHCO$_3$ (100 mL) and the reaction mixture was cooled in an ice/water bath. To the cold solution was added chloroacetyl chloride 2 (9.17 g, 81.2 mmol) dropwise over a period of 2 h. The mixture was allowed to warm to RT over 14 h. The mixture was extracted with ethyl acetate (3×50). The combined organic layers were dried over MgSO$_4$, filtered, and concentrated. The residue was triturated in ether and filtered to afford compound 3 as a white solid.

Part B.
Synthesis of N-(2,6-Dimethylphenyl)-piperazin-1-yl-acetamide (5):

To a solution of compound 3 (5 g, 25.2 mmol) in ethanol (100 mL) was added piperazine 4 (2.1 g, 25.0 mmol) and N,N-diisopropylethylamine (3.2 g, 25.2 mmol). The reaction mixture was refluxed for 24 h. The mixture was concentrated in vacuo and the residue was purified by column chromatography (10:1 DCM: MeOH) to afford compound 5.

Part C.
Synthesis of 5-(Oxiran-2-yl-methoxy)-2-1(3-trifluoromethyl)phenyl]benzoxazole (6):

1. Synthesis of 2-Amino4-methoxyphenol (12):

A solution of 4-methoxy-2-nitrophenol 11 (10 g, 59.1 mmol) and Pd/C (1.0 g) in methanol (100 ml) was placed on a Parr shaker under H$_2$ (50 psi) for 60 minutes. The reaction mixture was filtered through Celite 521 and the filter cake washed with MeOH. The filtrate was evaporated (in vacuo), to yield compound 12 as a tan solid.

2. Synthesis of 3-Trifluoromethyl-benzimidic Acid Ethyl Ester Hydrochloride (13):

To a solution of α,α,α-trifluoromethyl-m-tolunitrile 14 (1 g, 5.84 mmol) in EtOH (10 mL, anhydrous) was bubbled HCl (gas, anhydrous) for 10 minutes and the solution was stirred overnight. The solvent was evaporated to yield compound 13 as a white solid. The resulting solid was used in the next step without purification.

3. Synthesis of 5-Methoxy-2-(3-trifluoromethylphenyl)-benzoxazole (10):

A solution of compound 13 and compound 12 (850 mg, 6.13 mmol) in THF (10 mL) was heated to reflux and allowed to stir overnight. The reaction mixture was allowed to cool and the THF evaporated (in vacuo). The residue was dissolved in ethyl acetate and washed with water. The organic layer was dried over MgSO$_4$ and treated with activated carbon Norit A. The mixture was filtered through Celite 521, and evaporated (in vacuo) and the residue was purified using column chromatography (20% Ethyl acetatelhexanes) to afford compound 10 as a light yellow solid.

4. Synthesis of 2-[(3-Trifluoromethyl)phenyl]benzoxazol-5-ol (8):

To a solution of compound 10 (200 mg, 0.68 mmol) in CH$_2$Cl$_2$ (5 mL) was added BBr$_3$ (1M in CH$_2$Cl$_2$, 1 mL, 1 mmol) dropwise. The resulting solution was allowed to stir for 48 h. The solvent was removed by evaporation (in vacuo) and the residue was dissolved in ethyl acetate and washed with saturated NaHCO$_3$. The organic layer was dried over MgSO$_4$ and evaporated (in vacuo). The residue was purified using column chromatography (30% ethyl acetate/hexanes) to yield compound 8 as a white solid.

5. Synthesis of 5-(Oxiran-2-yl-methoxy)-2-[(3-trifluoromethyl)phenyl]benzoxazole (6):

To a suspension of NaH (7 mg, 60% dispersion in oil, 0.18 mmol) in DMF (2 mL, anhydrous) was added a solution of compound 8 (54 mg, 0.19 mmol) in DMF (2 mL, anhydrous) dropwise. The solution was allowed to stir for 15 minutes. To the above solution epichlorohydrin (50 μL, 0.63 mmol) was added and the resulting solution was allowed to stir overnight. The solvent was evaporated (in vacuo) and the residue dissolved in water and extracted with ethyl acetate. The organic layers were combined, dried over MgSO$_4$ and evaporated to yield compound 6 as a clear oil.

Part D.

Synthesis N-(2,6-Dimethylphenyl)-2-(4-{2-hydroxy-3-[2-(3-trifluoromethylphenyl)-benzoxazol-5-yloxy]-propyl}-piperazin-1-yl)acetamide (7):

A solution of compound 5 (183 mg, 0.73 mmol) and compound 6 in EtOH (2 mL) and triethylamine (0.2 mL) was heated to 90° C. and allowed to stir overnight. The reaction mixture was allowed to cool and the solvent evaporated (in vacuo) to yield an oil. The oil was purified by prep TLC (5/0.5/94.5 MeOH/NH$_4$OH/CH$_2$Cl$_2$) to yield compound 7 as a white Solid: Mass Spectrum (MH$^+$)=583.4

EXAMPLE 2

2-{4-13-(Benzothiazol-2-yloxy)-2-hydroxy-propyl]-piperazin-1-yl}-N-(2,6-dimethylphenyl)acetamide (43)

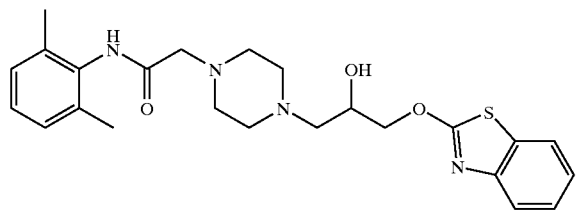

Synthesis of 2-(Oxiran-2-ylmethoxy)benzothiazole (44)

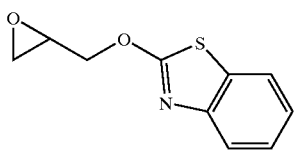

Compound 44 was prepared in the manner of compound 6 substituting 2-hydroxy-benzothiazole for compound 8 in partC-5 of Example 1.

Compound 43 was prepared in the manner of compound 7 substituting compound 44 for compound 6 in part D of compound 7: Mass Spectrum (MH+)=455.3.

EXAMPLE 3

N-(2,6-Dimethylphenyl)-2-{4-[2-hydroxy-3-(2-methyl-benzothiazol-5-yloxy)-propyl]-piperazin-1-yl}acetamide (45)

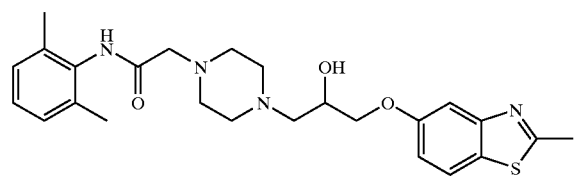

Synthesis of 2-Methyl-5-(oxiran-2-ylmethoxy)benzothiazole (33):

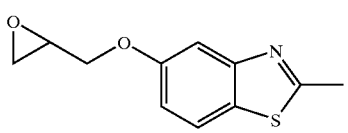

Compound 33 was prepared in the manner of compound 6 substituting 2-methyl-benzothiazol-5-ol for compound 8 in partC-5 of Example 1.

Compound 45 was prepared in the manner of compound 7 substituting compound 33 for compound 6 in part D of compound 7: Mass Spectrum (MH+)=469.3

EXAMPLE 4

4-(3-{4-1(2,6-Dimethylphenylcarbamoyl)-methyl-piperazin-1-yl}-2-hydroxy-propoxy)-1H-indole-2-carboxylic acid amide (46)

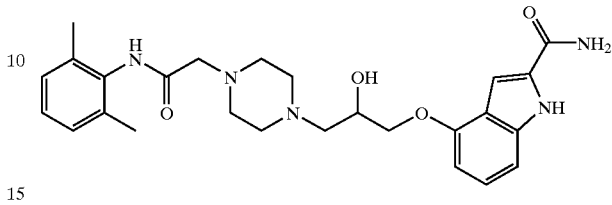

Compound 19 was prepared in the manner of compound 7 substituting the commercially available 4-glycidyloxy-2-indolecarboxamide for compound 6 in part D of compound 7: Mass Spectrum (MH+)=480.4.

EXAMPLE 5

2-{4-[3-(Benzothiazol-6-yloxy)2-hydroxy-propyl]-piperazin-1-yl}-N-(2,6dimethyl-phenyl)-acetamide (47)

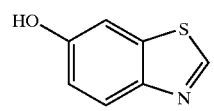

Synthesis of Benzothiazol-6-ol (16)

To a solution of 6-aminobenzothiazole (1.0 g, 6.66 mmol) in water (22 mL) and $H_2SO_4$ (16 mL) at 5° C. was added a solution of sodium nitrite (460 mg, 6.72 mmol) in water (13 mL) keeping the temperature below 5° C. The resulting solution was allowed to stir for 15 minutes. The reaction mixture was heated to 160° C. and a solution of $H_2SO_4$ (50 mL) and water (38 mL) was slowly added. The resulting mixture was allowed to stir for 1 h. The mixture was allowed to cool and an aqueous solution of 50% sodium hydroxide was added until the pH=7. The mixture was extracted with ethyl acetate and washed with brine. The combined organic was dried over $MgSO_4$ and evaporated to yield a semi-solid. The semi-solid was purified by column chromatography (40% ethyl acetate/hexanes) to yield benzothiazo-6-ol 16 as an off-white solid.

Synthesis of 6-(Oxiran-2-ylmethoxy)benzothiazole (48)

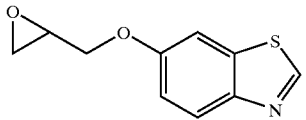

Compound 48 was prepared in the manner of compound 6 substituting compound 16 for compound 8 in partC-5 of Example 1.

Compound 47 was prepared in the manner of compound 7 substituting compound 48 for compound 6 in part D of compound 7: Mass Spectrum (MH$^+$)=455.3.

EXAMPLE 6

N-(2,6-Dimethylphenyl)-2-{4-[2-hydroxy-3-(2-methyl-benzothiazol-6-yloxy)-propyl]-piperazin-1-yl}aceamide (49)

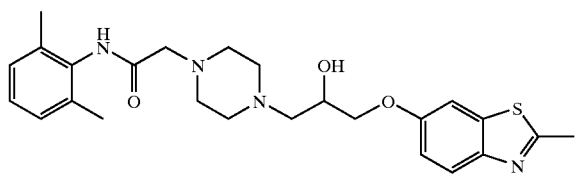

Synthesis of 2-Methylbenzothiazol-6-ol (50)

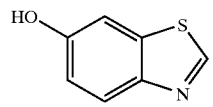

Compound 50 was prepared from the commercially available 6-methoxy-2-methyl-benzothiazole as described in partC-4 of Example 1.

Synthesis of 2-Methyl-6-(oxiran-2-ylmethoxy)benzothiazole (51)

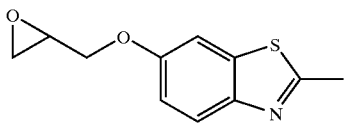

Compound 51 was prepared in the manner of compound 6 substituting compound 50 for compound 8 in partC-5 of Example 1.

Compound 49 was prepared in the manner of compound 7 substituting compound 51 for compound 6 in part D of compound 7: Mass Spectrum (MH$^+$)=469.3.

EXAMPLE 7

N-(2,6-Dimethylphenyl)-2-{4-[2-hydroxy-3-(2-methyl-benzothiazol-5-yloxy)-propyl]-3,5-dimethyl-piperazine-1-yl}acetamide (52)

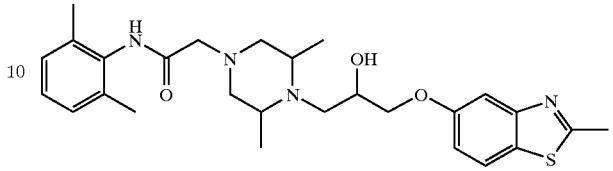

Synthesis of N-(2,6-Dimethylphenyl)-2-C3,5-dimethylpiperazin-1-yl)acetamide (53)

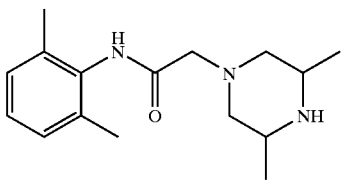

Compound 53 was prepared in the manner of compound 3 substituting 2,6-dimethylpiperazine for piperazine in part A of Example 1.

Compound 52 was prepared in the manner of compound 7 substituting compound 33 for compound 6 and compound 53 for compound 5 in part D of compound 7: Mass Spectrum (MH$^+$)=497.4.

EXAMPLE 8

2-{4-[2-Hydroxy-3-(2-methyl-benzothiazol-5-yloxy)-propyl]-piperazin-1-yl}-N-(4-hydroxy-phenyl)acetamide (54)

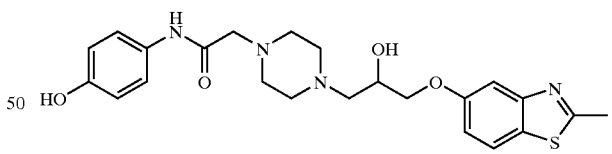

Synthesis of 4-Aminophenyl Acetate (55)

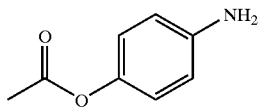

Compound 55 was prepared in the manner of compound 12 substituting 4-nitrophenyl acetate for compound 11 in part C-1 of Example 1.

Synthesis of 4-(2-Chloroacetylamino)phenyl Acetate (56)

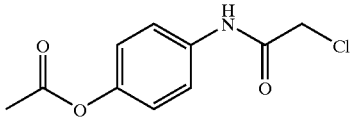

Compound 56 was prepared in the manner of compound 3 substituting compound 55 for compound 1 in part A of Example 1.

Synthesis of 4-(2-Piperazinylacetylamino)phenyl Acetate(57)

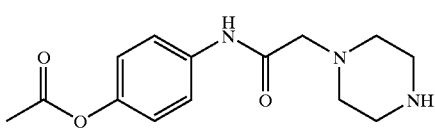

Compound 57 was prepared as described in part B of Example 1 substituting compound 56 for compound 3.

Compound 54 was prepared in the manner of compound 7 substituting compound 33 for compound 6 and compound 57 for compound 5 in part D of compound 7: Mass Spectrum (MH$^+$)=457.5.

EXAMPLE 9

N-(2,6-Dimethylphenyl)-2-{4-[2-hydroxy-3-(2-phenyl-benzothiazol-5-yloxy)-propyl]-piperazin-1-yl}acetamide (58)

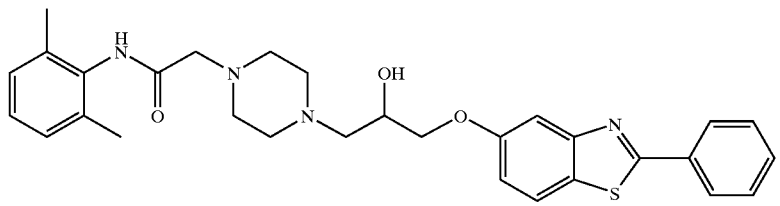

Synthesis of Phenyl-N-13-(phenylmethoxy)phenyl] carboxamide (25)

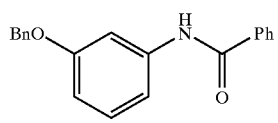

To a solution of 3-benzyloxyaniline 23 (1.0 g, 5.0 mmol) and TEA (0.74 mL, 5.3 mmol) in CH$_2$Cl$_2$ was added benzoyl chloride (0.61 mL, 5.26 mmol) dropwise and the mixture was allowed to stir overnight. The reaction mixture was diluted with water and the resulting solid was collected by vacuum filtration. The solid was allowed to air dry, to yield compound 25 as a white solid.

Synthesis of Phenyl{[(3-phenylmethoxy)phenyl]amino}methane-1-thione (26)

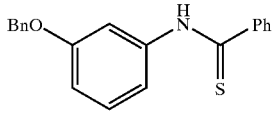

A solution of compound 25 (455 mg, 1.5 mmol) and Lawesson's reagent (0.6 mol equiv) in chlorobenzene (15 mL) was heated to 120° C. and allowed to stir for 1.5 h. The reaction was allowed to cool and the solvent was evaporated (in vacuo). The residue was purified by column chromatography (ethyl acetate/hexane 1:9) to yield compound 26 as a yellow solid.

Synthesis of 2-Phenyl-5-(phenylmethoxy)benzothiazole (27)

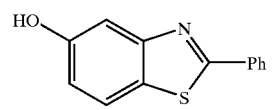

To a solution of compound 26 (960 mg, 3 mmol) in ethanol (5 mL) was added an aqueous sodium hydroxide solution (30%, 8 mol equiv). The mixture was diluted with water (6 mL) to give a final solution of 10% aqueous sodium hydroxide. The resulting solution was added to a stirred solution of potassium ferricyanide (4 mol equiv) in water at 90° C. in aliquots (1 mL) and the resulting mixture was heated for 30 min. The reaction mixture was allowed to cool and the product was extracted with ethyl acetate. The organic layer was dried and evaporated. The residue, a mixture of 27 and 28, was column purified (ethyl acetate/hexane—1:99) to provide compound 27 as a white solid.

Synthesis of 2-Phenylbenzothiazol-5-ol (29)

Palladium hydroxide (100 mg) was added to a solution of 27 (260 mg, 0.8 mmol) of ethanol/cyclohexene (5 mL/2 mL) followed by warming for reflux for 16 h. The reaction mixture was cooled and the catalyst was removed by filtration (through Celite). The solvent was evaporated to provide compound 29 as a white solid.

Synthesis of 5-(Oxiran-2-ylmethoxy)-2-phenylbenzothiazole (59)

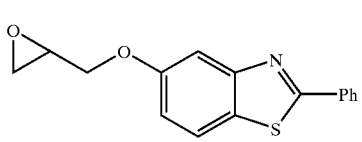

Compound 59 was prepared in the manner of compound 6 substituting compound 29 for compound 8 in partC-5 of Example 1.

Compound 58 was prepared in the manner of compound 7 substituting compound 59 for compound 6 in part D of compound 7: Mass Spectrum (MH$^+$)=531.6

EXAMPLE 10

N-(2,6-Dimethylphenyl)-2-{4-[2-hydroxy-3-(2-phenyl-benzoxazol-5-yloxy)-propyl]-piperazin-1-yl}acetamide (60)

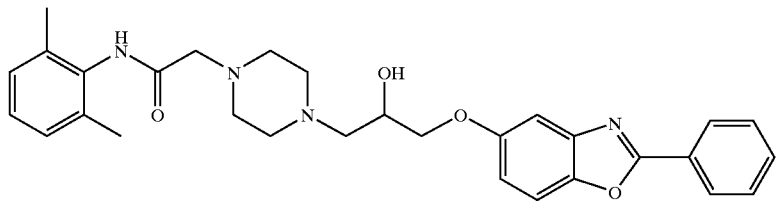

Synthesis of 5-(Oxiran-2-ylmethoxy)-2-phenylbenzoxazole (61)

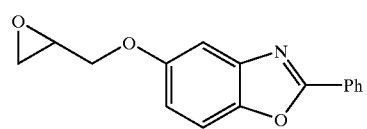

Compound 61 was prepared in the manner of compound 6 substituting ethyl benzimidate hydrochloride for compound 13 in partC 1–5 of Example 1.

Compound 60 was prepared in the manner of compound 7 substituting compound 61 for compound 6 in part D of compound 7: Mass Spectrum (MH$^+$)=515.3.

EXAMPLE 11

N-(2,6-Dimethylphenyl)2-{4-[2-hydroxy-3-(2-phenyl-benzothiazol-7-yloxy)-propyl]-piperazin-1-ylacetamide (62)

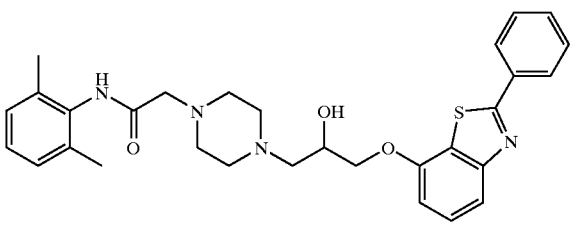

Synthesis of 7-(Oxiran-2-ylmethoxy)-2-phenylbenzothiazole (63)

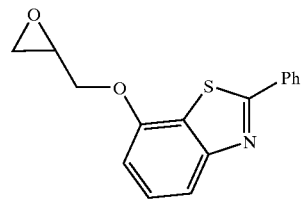

Compound 63 was prepared in the manner of compound 59 substituting deprotected compound 28 for compound 29 in example 9.

Compound 62 was prepared in the manner of compound 7 substituting compound 63 for compound 6 in part D of compound 7: Mass Spectrum (MH$^+$)=531.3.

EXAMPLE 12

N-(2,6-Dimethylphenyl)-2-{4-[2-hydroxy-3-(2-methyl-benzothiazol-5-yloxy)-propyl]-2-oxo-piperazin-1-yl}acetamide (64)

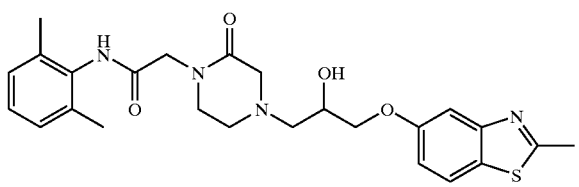

Synthesis of Phenylmethyl 4-{[N-(2,6-Dimethylphenyl)carbamoyl]methyl}-3-oxopiperazinecarboxylate (31)

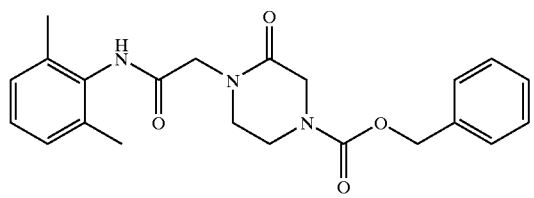

To a solution of compound 30 (252 mg, 1.3 mmol) in THF (13 mL) and NaH (62 mg, 1.6 mmol) was added Compound 3 (300 mg, 1.3 mmol). The solution was allowed to stir under nitrogen overnight. The reaction was quenched with water (0.1 mL) and dried over Na$_2$SO$_4$ The solution was concentrated and purified using column chromatography conditions to yield compound 31 as a solid.

Synthesis of N-(2,6-Dimethylphenyl)-2-(2-oxopiperazinyl)-acetamide (32)

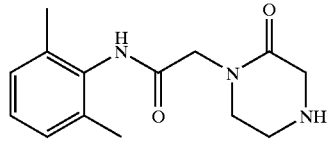

To a solution of compound 31 in methanol (10 mL) 10% palladium on carbon was added. The reaction vessel was charged with hydrogen (40 p.s.i) and agitated for 4 h. The catalyst was removed by filtration and the filtrate was concentrated and purified using column chromatography (1:15 MeOH:DCM) to yield compound 32 as a semi solid.

Compound 64 was prepared in the manner of compound 7 substituting compound 33 for compound 6 and compound 32 for compound 5 in part D of compound 7: Mass Spectrum (MH$^+$)=483.3

EXAMPLE 13

N-(2,6-Dimethylphenyl)-2-{4-[2-hydroxy-3-(2-methyl-benzoxazol-5-yloxy)-propyl]-piperazin-1-yl}acetamide (65)

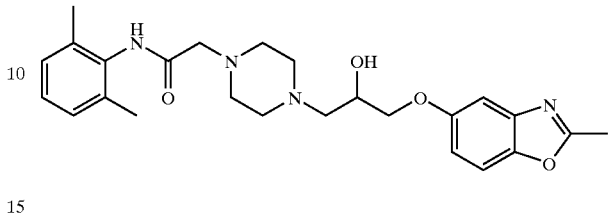

Synthesis of 5-Methoxy-2-methyl-benzoxazole (19)

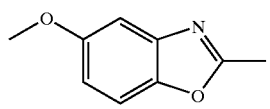

A solution of 2-amino-4-methoxyphenol 17 (8 g, 57.4 mmol) in trimethyl orthoacetate 18 (50 mL) was heated to reflux and allowed to stir for 24 h. The reaction was allowed to cool and the excess 18 was evaporated (in vacuo). The residue was dissolved in ethyl acetate and washed with water. The organic layer was dried over MgSO$_4$ and treated with activated carbon Norit A. The resulting solution was filtered through Celite 521 and evaporated to yield an oil. The oil was chromatographed on silica gel (20% ethyl acetate:hexanes) to yield compound 19 as a light yellow solid.

Synthesis of 2-Methyl-5-oxiran-2-ylmethoxybenzoxazole (67)

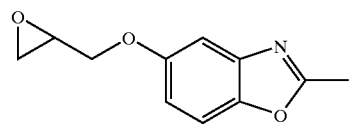

Compound 67 was prepared in the manner of compound 6 substituting 6-hydroxy-2-methyl-benzoxazole 66 for compound 8 in part C-5 of Example 1.

Compound 66 in turn was obtained by the deprotection of compound 19 as described in partC-4 of Example 1.

Compound 65 was prepared in the manner of compound 7 substituting compound 67 for compound 6 in part D of compound 7: Mass Spectrum (MH$^+$)=543.4

EXAMPLE 14

N-(2,6-Dimethylphenyl)-2-(4-{2-hydroxy-3-12-(4-trifluoromethyl-phenyl)-benzoxazol-5-yloxyl-propyl}-piperazin-1-yl)acetamide (68)

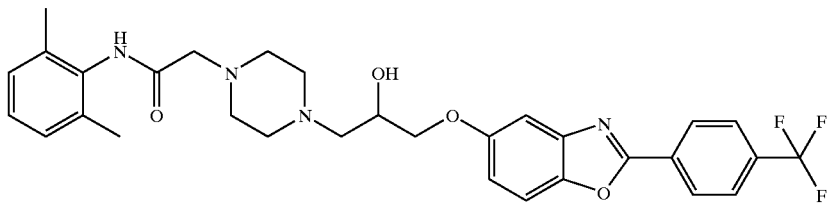

Synthesis of 5-(Oxiran-2-ylmethoxy)-2-(4-trifluoromethyl-phenyl)benzoxazole (69)

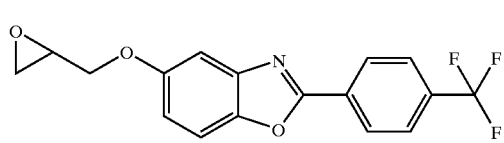

Compound 69 was prepared in the manner of compound 6 substituting 4-trifluoromethylbenzimidic acid ethyl ester hydrochloride for compound 13 in partC1-5 of Example 1.

Compound 68 was prepared in the manner of compound 7 substituting compound 69 for compound 6 in part D of compound 7: Mass Spectrum (MH$^+$)=583.4

EXAMPLE 15

N-(2,6-Dimethylphenyl)-2-{4-[2-hydroxy-3-(quinoxalin-2-yloxy)-propyl]-piperazin-1-yl}acetamide (70)

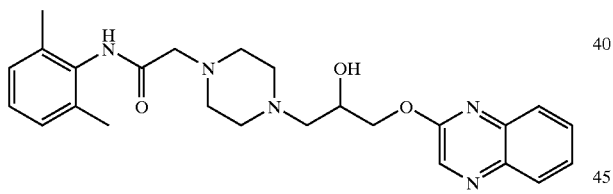

Synthesis of 2-(Oxiran-2-ylmethoxy)quinoxaline (71)

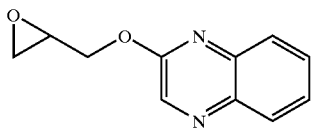

Compound 71 was prepared in the manner of compound 6 substituting quinoxaline-2-ol for compound 8 in part C-5 of Example 1.

Compound 70 was prepared in the manner of compound 7 substituting compound 71 for compound 6 in part D of compound 7: Mass Spectrum (MH$^+$)=450.9.

EXAMPLE 16

N-(2,6-Dimethylphenyl)-2-{4-[2-hydroxy-3-(pyridin-3-yloxy)-propyl]-piperazin-1-yl}acetamide (72)

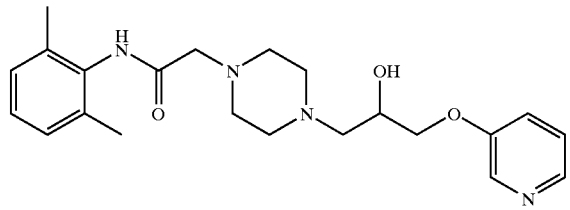

Synthesis of 3-(Oxiran-2-ylmethoxy)pyridine (73)

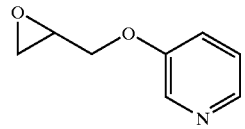

Compound 73 was prepared in the manner of compound 6 substituting 3-hydroxy-pyridine for compound 8 in part C-5 of Example 1.

Compound 72 was prepared in the manner of compound 7 substituting compound 73 for compound 6 in part D of compound 7: Mass Spectrum (MH$^+$)=399.4.

EXAMPLE 17

N-(2,6-Dimethylphenyl)-2-{4-[2-hydroxy-3-(quinolin4-yloxy)-propyl]-piperazin-1-yl}acetamide (74)

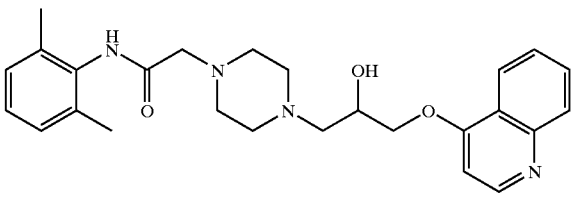

Synthesis of 4-(Oxiran-2-ylmethoxy)quinoline (75)

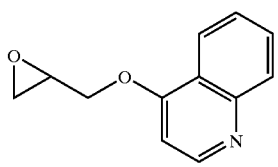

Compound 75 was prepared in the manner of compound 6 substituting 4-hydroxy-quinoline for compound 8 in part C-5 of Example 1.

Compound 74 was prepared in the manner of compound 7 substituting compound 75 for compound 6 in part D of compound 7: Mass Spectrum (MH$^+$)=449.4.

EXAMPLE 18

N-(2,6-Dimethylphenyl)-2-{4-[2-hydroxy-3-(isoquinolin-5-yloxy)-propyl]-piperazin-1-yl}acetamide (76)

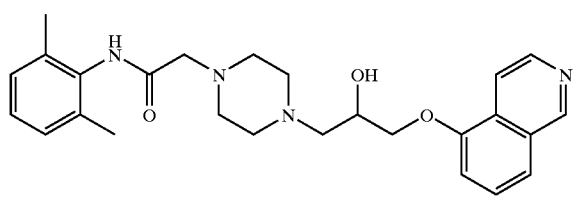

Synthesis of 5-(Oxiran-2-ylmethoxy)isoquinoline (77)

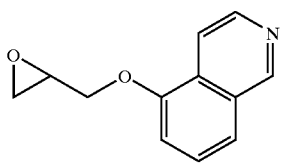

Compound 77 was prepared in the manner of compound 6 substituting 5-hydroxy-isoquinoline for compound 8 in part C-5 of Example 1.

Compound 76 was prepared in the manner of compound 7 substituting compound 77 for compound 6 in part D of compound 7: Mass Spectrum (MH$^+$)=449.4.

EXAMPLE 19

N-(2,6-Dimethylphenyl)-2-{4-[2-hydroxy-3-(quinolin-6-yloxy)-propyl]-piperazin-1-yl}acetamide (78)

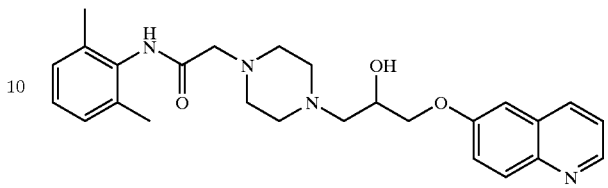

Synthesis of 6-(Oxiran-2-ylmethoxy)quinoline (79)

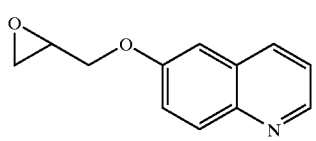

Compound 79 was prepared in the manner of compound 6 substituting 6-hydroxy-quinoline for compound 8 in part C-5 of Example 1.

Compound 78 was prepared in the manner of compound 7 substituting compound 79 for compound 6 in part D of compound 7: Mass Spectrum (MH$^+$)=449.4

EXAMPLE 20

N-(2,6-Dimethylphenyl)-2-{4-[2-hydroxy-3-(2-methyl-quinolin-7-yloxy)-propyl]-piperazin-1-yl}acetamide (80)

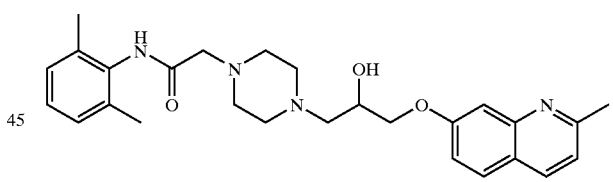

Synthesis of 2-Methyl-7-(oxiran-2-ylmethoxy)quinoline (81)

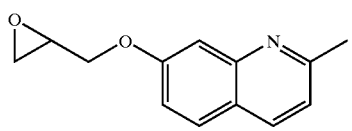

Compound 81 was prepared in the manner of compound 6 substituting 7-hydroxy-2-methyl-quinoline for compound 8 in part C-5 of Example 1.

Compound 80 was prepared in the manner of compound 7 substituting compound 81 for compound 6 in part D of compound 7: Mass Spectrum (MH$^+$)=463.5.

EXAMPLE 21

2-{4-[3-(Benzothiazol-2-ylamino)-2-hydroxypropyl]piperazinyl}-N-(2,6-dimethylphenyl)acetamide (39)

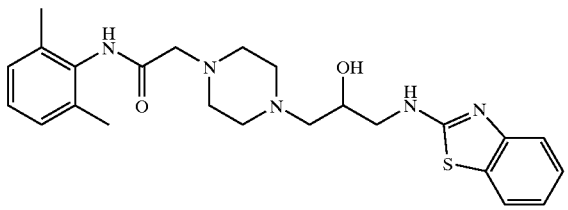

39

Synthesis of (Phenylmethoxy)-N-prop-2-enylcarboxamide (42)

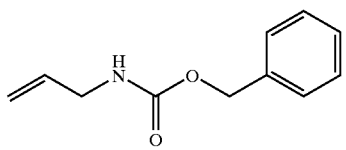

42

To a solution of allylamine (3.34 g, 5.85 mmol) in dichloromethane (100 mL) and triethylamine (16 mL) benzyl chloroformate (8.25 mL, 5.78 mmol) was added at 0° C. The mixture was stirred at 0° C. for 2 hours and additional 90 minutes at RT. The solvent was removed by evaporation and the residue was purified by flash column chromatography (30% EtOAc/Hexanes) to yield compound 42 as a clear oil.

Synthesis of N-(Oxiran-2-ylmethoxy)(phenylmethoxy)carboxamide (35)

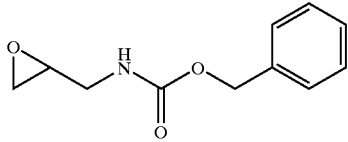

35

Compound 42 (5.0 g, 2.61 mmol) was treated with m-chloroperbenzoic acid (11.71 g, 9.1 mmol) in dichloromethane (110 mL) at room temperature for 18 h. Dichloromethane was evaporated to afford a viscous oil which was then purified by flash column chromatography (30%EtOAc/Hexanes) to give compound 35 as a clear oil.

Synthesis of N-(2,6-Dimethylphenyl)-2-(4-{2-hydroxy-3-[phenylmethoxyl carbonylaminol propyl}piperazinyl)acetamide (36)

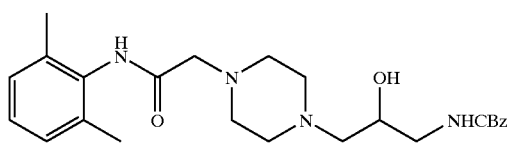

36

A solution of compound 42 (2.5 g, 1.2 mmol) and compound 5 (5.94 g, 2.4 mmol) in ethanol (100 mL) and triethylamine (3.34 mL) was refluxed for 18 h. Solvents were removed and the residue was purified by flash column chromatography (ethyl acetate) to afford compound 36 as a white solid.

Synthesis of 2-[4-(3-Amino-2-hydroxypropyl)piperazinyl]-N-(2,6-dimethylphenyl)acetamide (37)

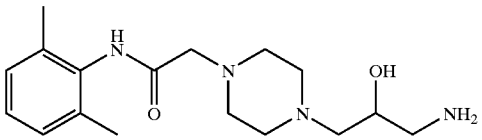

37

A solution of compound 36 (3.0 g, 0.66 mmol) in methanol (70 mL) in presence of 10% Palladium on Carbon (0.337 g) was stirred under hydrogen atmosphere for 16 h. Filtration of catalyst followed by concentration afforded compound 37 as a sticky solid.

To a solution of compound 37 (75 mg) in ethanol (2 mL) was added triethylamine (0.13 mL) and 2-chlorobenzthiazole (87 mg) followed by warming to reflux for 16 h. The reaction mixture was concentrated and purified by preparative TLC (5%MeOH/Dichloromethane) to give Compound 39 as a white solid. Mass Spectrum (MH$^+$)= 454.4.

EXAMPLE 22

2-{4-[3-(Benzoxazol-2-ylamino)-2-hydroxypropyl]piperazinyl}-N-(2,6-dimethylphenyl)acetamide (82)

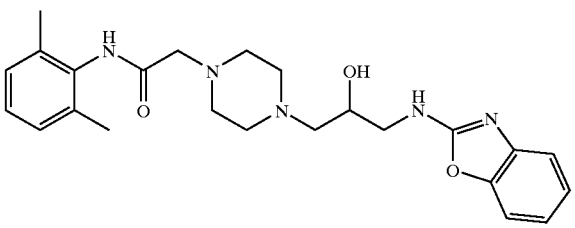

82

Compound 82 was prepared in the manner of compound 39 by substituting 2-chloro-benzoxazole for 2-chloro-benzothiazole as in example 21. Mass Spectrum (MH$^+$)= 438.4.

EXAMPLE 23

Mitochondrial Assays

Rat heart mitochondria were isolated by the method of Nedergard and Cannon (Methods in Enzymol. 55, 3, 1979).

Palmitoyl CoA oxidation—The Palmityl CoA oxidation was carried out in a total volume of 100 micro liters containing the following agents: 110 mM KCl, 33 mM Tris buffer at pH 8, 2 mM KPi, 2 mM MgCl$_2$, 0.1 mM EDTA, 14.7 microM defatted BSA, 0.5 mM malic acid, 13 mM carnitine, 1 mM ADP, 52 micrograms of mitochondrial protein, and 16 microM 1-C14 palmitoyl CoA (Sp. Activity 60 mCi/mmole; 20 microCi/ml, using 5 microliters per assay). The compounds of this invention were added in a DMSO solution at the following concentrations: 100 microM, and 50 microM. In each assay, a DMSO control was used. After 15 min at 30° C., the enzymatic reaction was centrifuged (20,000 g for 1 min), and 70 microliters of the supernatant was added to an activated reverse phase silicic acid column (approximately 0.5 ml of silicic acid). The column was eluted with 2 ml of water, and 0.5 ml of the eluent was used for scintillation counting to determine the amount of $C^{14}$ trapped as $C^{14}$ bicarbonate ion.

TABLE 1

Inhibition of mitochondrial fatty acid oxidation using palmitoyl CoA as substrate - percent of inhibition at two concentrations and $IC_{50}$.

| Compound # | 100 μm (%) | 50 μm (%) | $IC_{50}$ (μm) |
|---|---|---|---|
| 7 | — | 77 | — |
| 39 | 27 | — | — |
| 43 | 21 | — | — |
| 45 | 87 | — | ~20 |
| 46 | 61 | — | ~125 |
| 47 | 70 | — | ~125 |
| 49 | 3 | — | — |
| 52 | 95 | — | ~1 |
| 54 | 81 | — | ~8 |
| 60 | — | 61 | — |
| 62 | — | 62 | — |
| 64 | 41 | — | — |
| 68 | — | 68 | — |
| 70 | 12 | — | — |
| 72 | 8 | — | — |
| 74 | 12 | — | — |
| 76 | 26 | — | — |
| 78 | 42 | — | — |
| 80 | 22 | — | — |
| 82 | 22 | — | — |

EXAMPLE 25

Metabolic Stability: As a measure of metabolic stability the compounds of this invention were incubated with human liver S-9 microsomal fractions. After, 30 minutes at 37 C, the amount of parent drug remaining was determined using LC-mass spec. The response factors for each compound was determined by establishing a standard curve and using an internal standard during the analysis of the samples. An average of five experiments for percentage of ranolazine remaining at the 30 minute time point is 57%. The compounds of this invention were assayed as described in the protocol below and the percentage of parent remaining was divided by the average % of ranolazine remaining (57%) affording a metabolic stability factor. A compound with a stability number greater than 1.2 has a better stability than ranolazine in the liver S-9 assay. A compound with a stability number between 1.2 and 0.8 has an equivalent stability in the liver S-9 assay. A compound with a stability number less than 0.8 is less stable than ranolazine in the liver S-9 assay.

The purpose of this experiment is to compare the percentages remaining for compounds of this invention with the percentage remaining for ranolazine after 30 minutes of incubation with human liver S9 fractions.

Reagents:

The following reagents were used; Potassium phosphate, 0.5M pH 7.4 (incubation buffer), kept at room temperature; 0.05M $MgCl_2$ kept at 4° C.; β-Nicotinamide adenine dinucleotide phosphate, tetrasodium salt, reduced form (NADPH), 0.02M solution in water (~16.6 mg/mL) from Sigma Lot # 79H7044 prepared on day of use. 1 mM of ranolazine or Compounds 43, 45, 47, 52, 70, 74, 76, 78, and 80 in ACN further diluted to obtain 100 μM in 10% ACN; Human S9 stock: 20 mg/mL from Gentest.

Procedure:
Incubation mixtures were prepared as follows:

TABLE 2

| Component | Volume per 0.25 mL of Incubation Mixture | Final concentration |
|---|---|---|
| 10 μM CVT compounds | 25 μL | 10 μM |
| $MgCl_2$ | 25 μL | 0.005 M |
| NADPH | 25 μL | 0.002 M |
| S9 | 25 μL | 2 mg/mL |
| Incubation Buffer | 25 μL | 0.05 M |
| Water | 125 μL | — |

*1% organic solvent (acetonitrile) was used in incubation mixture.
Generally, 30 incubates were prepared at a time by pre-mixing 0.75 mL of $MgCl_2$, 0.75 mL of incubation buffer, 0.75 mL of NADPH, 3.75 mL of water. Then pipette 200 μL/incubate, add 25 μL of compound being tested, mix, and initiate reaction by addition of S-9.

Combine all components with incubation buffer and re-pipette 200 μL/tube+25 μL of the compound being tested along with 25 μL of S-9.

After 5 min of pre-incubation at 37° C., at 0 and 30 min after starting the reaction, a 50 μl aliquot of the incubation mixture was removed and added to 100 μL of 9:1 acetonitrile: methanol containing the internal standard.

The mixture was centrifuged and a 100 μL aliquot of the supernatant was diluted in 1 mL of solvent C (0.1% Formic Acid in water). Then samples were analyzed for change between the ratio of compound to internal standard at time zero and 30 minutes by LC/MS (injected 10 μL).

Analytical and Data Calculations:

Samples were analyzed for the starting compounds and potential metabolite/s by LC/MS using an internal standard and an ODS-C18 column with a flow rate of 0.25 ml/min. Following the above procedure resulted in the following relative stability factors as compared to ranolize for the compounds of this invention as illustrated in Table 3.

TABLE 3

| Compound # | Liver S9 Stability Factor |
|---|---|
| 43 | 0.6 |
| 45 | 0.8 |
| 46 | 1.1 |
| 47 | 1.5 |
| 52 | 0.5 |
| 70 | 0.1 |
| 74 | 1.0 |
| 76 | 0.8 |
| 78 | 0.6 |
| 80 | 0.5 |

We claim:
1. A substituted piperazine compound having the following formula:

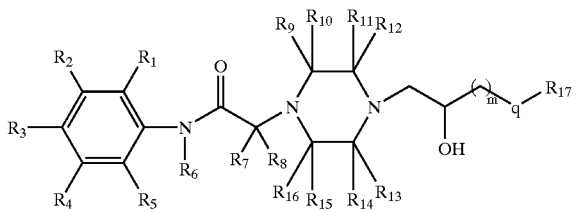

wherein m=1, 2, or 3;
q=NH, O, or S;
$R_1$, $R_2$, $R_3$, $R_4$ and $R_5$ are each independently selected from the group consisting of hydrogen, $OR^{20}$ and $C_{1-15}$ straight or branched alkyl;

$R_6$, $R_7$ and $R_8$ are each independently hydrogen;

$R_9$, $R_{10}$, $R_{11}$, $R_{12}$, $R_{13}$, $R_{14}$, $R_{15}$ and $R_{16}$ are each independently selected from the group consisting of hydrogen and $C_{1-4}$ straight or branched alkyl, or wherein $R_9$ and $R_{10}$ may together form a carbonyl, or $R_{11}$ and $R_{12}$ may together form a carbonyl, or $R_{13}$ and $R_{14}$ may together form a carbonyl, or $R_{15}$ and $R_{16}$ may together form a carbonyl;

$R_{17}$ is selected from the group consisting of benzoxazolyl, benzothiazolyl, quinoxalinyl, pyridinyl, quinolinyl, isoquinolinyl, and indolyl, wherein each group is optionally substituted with from 1 to 3 substituents selected from the group consisting of $CON(R^{20})_2$, $C_{1-15}$ straight or branched alkyl and aryl, wherein the aryl substituents are optionally substituted with 1 substituent selected from the group consisting of $CF_3$; and $R^{20}$ is hydrogen.

2. The compound of claim 1 wherein q=NH or O;

$R_1$, $R_2$, $R_3$, $R_4$ and $R_5$ are each independently selected from the group consisting of hydrogen, $OR^{20}$ and $C_{1-8}$ straight or branched alkyl;

$R_6$, $R_7$ and $R_8$ are each independently hydrogen;

$R_9$, $R_{10}$, $R_{11}$, $R_{12}$, $R_{13}$, $R_{14}$, $R_{15}$ and $R_{16}$ are each independently selected from the group consisting of hydrogen and $C_{1-4}$ straight or branched alkyl, or wherein $R_9$ and $R_{10}$ may together form a carbonyl, or $R_{11}$ and $R_{12}$ may together form a carbonyl, or $R_{13}$ and $R_{14}$ may together form a carbonyl, or $R_{15}$ and $R_{16}$ may together form a carbonyl;

$R_{17}$ is selected from the group consisting of benzoxazolyl, benzothiazoly, quinoxalinyl, pyridinyl, quinolinyl, isoquinolinyl, and indolyl, wherein each group is optionally substituted with from 1 to 3 substituents selected from the group consisting of $CON(R^{20})_2$, $C_{1-15}$ straight or branched alkyl and aryl, wherein the aryl substituents are optionally substituted with 1 substituent selected from the group consisting of $CF_3$; and $R^{20}$ is hydrogen.

3. The compound of claim 1 wherein $R_1$, $R_2$, $R_3$, $R_4$ and $R_5$ are each independently selected from the group consisting of hydrogen, $OR^{20}$ and $C_{1-5}$ straight or branched alkyl;

$R_6$, $R_7$ and $R_8$ are each independently hydrogen;

$R_9$, $R_{10}$, $R_{11}$, $R_{12}$, $R_{13}$, $R_{14}$, $R_{15}$ and $R_{16}$ are each independently selected from the group consisting of hydrogen and $C_{1-4}$ straight or branched alkyl, or wherein $R_9$ and $R_{10}$ may together form a carbonyl, or $R_{11}$ and $R_{12}$ may together form a carbonyl, or $R_{13}$ and $R_{14}$ may together form a carbonyl, or $R_{15}$ and $R_{16}$ may together form a carbonyl;

$R_{17}$ is selected from the group consisting of benzoxazolyl, benzothiazolyl, quinoxalinyl, pyridinyl, quinolinyl, isoquinolinyl, and indolyl, wherein each group is optionally substituted with from 1 to 2 substituents selected from the group consisting of $CON(R^{20})_2$, $C_{1-8}$ straight or branched alkyl and aryl, wherein the aryl substituents are optionally substituted with 1 substituent selected from the group consisting of $CF_3$; and $R^{20}$ is hydrogen.

4. The compound of claim 1 wherein $R_1$, $R_2$, $R_3$, $R_4$ and $R_5$ are each independently selected from the group consisting of hydrogen, $OR^{20}$ and $C_{1-3}$ straight or branched alkyl;

$R_6$, $R_7$ and $R_8$ are each independently hydrogen;

$R_9$, $R_{10}$, $R_{11}$, $R_{12}$, $R_{13}$, $R_{14}$, $R_{15}$ and $R_{16}$ are each independently selected from the group consisting of hydrogen and $C_{1-2}$ alkyl or wherein $R_9$ and $R_{10}$ may together form a carbonyl, or $R_{11}$ and $R_{12}$ may together form a carbonyl, or $R_{13}$ and $R_{14}$ may together form a carbonyl, or $R_{15}$ and $R_{16}$ may together form a carbonyl;

$R_{17}$ is selected from the group consisting of benzoxazolyl, benzothiazolyl, quinoxalinyl, pyridinyl, quinolinyl, isoquinolinyl, and indolyl, wherein each group is optionally substituted with from 1 to 2 substituents selected from the group consisting of $CON(R^{20})_2$, $C_{1-5}$ straight or branched alkyl and aryl, wherein the aryl substituents are optionally substituted with 1 substituent selected from the group consisting of $CF_3$; and $R^{20}$ is hydrogen.

5. The compound of claim 1 wherein m=1;

$R_1$, $R_2$, $R_3$, $R_4$ and $R_5$ are each independently selected from the group consisting of hydrogen, $OR_{20}$ and $C_{1-3}$ straight or branched alkyl;

$R_6$, $R_7$ and $R_8$ are each independently hydrogen;

$R_9$, $R_{10}$, $R_{11}$, $R_{12}$, $R_{13}$, $R_{14}$, $R_{15}$ and $R_{16}$ are each independently selected from the group consisting of hydrogen and methyl, or wherein $R_9$ and $R_{10}$ may together form a carbonyl, or $R_{11}$ and $R_{12}$ may together form a carbonyl, or $R_{13}$ and $R_{14}$ may together form a carbonyl, or $R_{15}$ and $R_{16}$ may together form a carbonyl;

$R_{17}$ is selected from the group consisting of benzoxazolyl, benzothiazolyl, quinoxalinyl, pyridinyl, quinolinyl, isoquinolinyl, and indolyl, wherein each group is optionally substituted with from 1 to 2 substituents selected from the group consisting of $CON(R^{20})_2$, $C_{1-3}$ straight or branched alkyl and aryl, wherein the aryl substituents are optionally substituted with 1 substituent independently selected from the group consisting of $CF_3$; and $R^{20}$ is hydrogen.

6. The compound of claim 1 wherein $R_{17}$ is selected from the group consisting of benzoxazolyl, benzothiazolyl, and indolyl, wherein each group is optionally substituted with from 1 to 3 substituent selected from the group consisting of $CON(R^{20})_2$, $C_{1-15}$ straight or branched alkyl and aryl, wherein the aryl substituents are optionally substituted with 1 substituent independently selected from the group consisting of $CF_3$.

7. The compound of claim 6 wherein q=NH, O;

$R_1$, $R_2$, $R_3$, $R_4$ and $R_5$ are each independently selected from the group consisting of hydrogen, $OR^{20}$ and $C_{1-8}$ straight or branched alkyl;

$R_6$, $R_7$ and $R_8$ are each independently hydrogen;

$R_9$, $R_{10}$, $R_{11}$, $R_{12}$, $R_{13}$, $R_{14}$, $R_{15}$ and $R_{16}$ are each independently selected from the group consisting of hydrogen and $C_{1-4}$ straight or branched alkyl or wherein $R_9$ and $R_{10}$ may together form a carbonyl, or $R_{11}$ and $R_{12}$ may together form a carbonyl, or $R_{13}$ and $R_{14}$ may together form a carbonyl, or $R_{15}$ and $R_{16}$ may together form a carbonyl;

$R_{17}$ is selected from the group consisting of benzoxazolyl, benzothiazolyl, and indolyl, wherein each group is optionally substituted with 1–3 substituents selected from the following $CON(R_{20})_2$, $C_{1-15}$ straight or branched alkyl and aryl, wherein the aryl substituents are optionally substituted with 1 substituent selected from the group consisting of $CF_3$; and $R^{20}$ is hydrogen.

8. The compound of claim 6 wherein q=NH or O;

$R_1$, $R_2$, $R_3$, $R_4$ and $R_5$ are each independently selected from the group consisting of hydrogen, $OR_{20}$ and $C_{1-5}$ straight or branched alkyl;

$R_6$, $R_7$ and $R_8$ are each independently hydrogen;

$R_9$, $R_{10}$, $R_{11}$, $R_{12}$, $R_{13}$, $R_{14}$, $R_{15}$ and $R_{16}$ are each independently selected from the group consisting of hydrogen and $C_{1-3}$ straight or branched alkyl, or wherein $R_9$ and $R_{10}$ may together form a carbonyl, or $R_{11}$ and $R_{12}$ may together form a carbonyl;

$R_{17}$ is selected from the group consisting of benzoxazolyl, benzothiazolyl, and indolyl, wherein each group is optionally substituted with from 1 to 2 substituents selected from the group consisting of $CON(R^{20})_2$, $C_{1-8}$ straight or branched alkyl and aryl, wherein the aryl substituents are optionally substituted with 1 substituent independently selected from the group consisting of $CF_3$; and $R^{20}$ is hydrogen.

9. The compound of claim 6 wherein q=NH or O;

$R_1$, $R_2$, $R_3$, $R_4$ and $R_5$ are each independently selected from the group consisting of hydrogen, $OR^{20}$ and $C_{1-3}$ straight or branched alkyl;

$R_6$, $R_7$ and $R_8$ are each independently hydrogen;

$R_9$, $R_{10}$, $R_{11}$, $R_{12}$, $R_{13}$, $R_{14}$, $R_{15}$ and $R_{16}$ are each independently selected from the group consisting of hydrogen and $C_{1-3}$ straight or branched alkyl, or wherein $R_9$ and $R_{10}$ may together form a carbonyl;

$R_{17}$ is selected from the group consisting of benzoxazolyl, benzothiazolyl, and indolyl, wherein each group is optionally substituted with from 1 to 2 substituents selected from the group consisting of $CON(R_{20})_2$, $C_{1-4}$ straight or branched alkyl and aryl, wherein the aryl substituents are optionally substituted with 1 substituent selected from the group consisting of $CF_3$; and $R^{20}$ is hydrogen.

10. A substituted piperazine compound having the following formula:

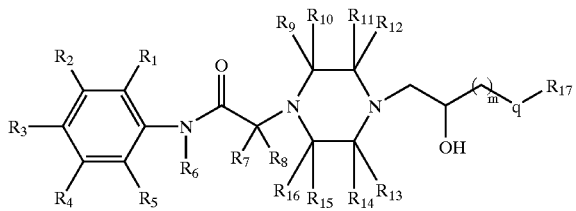

wherein q=NH or O;

m=1, 2 or 3;

$R_1$, $R_2$, $R_3$, $R_4$ and $R_5$ are each independently selected from the group consisting of hydrogen, $OR^{20}$, and $C_{1-3}$ straight or branched alkyl;

$R_6$, $R_7$ and $R_8$ are each independently hydrogen;

$R_9$, $R_{10}$, $R_{11}$, $R_{12}$, $R_{13}$, $R_{14}$, $R_{15}$ and $R_{16}$ are each independently selected from the group consisting of hydrogen, and $C_{1-2}$ alkyl, or wherein $R_9$ and $R_{10}$ may together form a carbonyl;

$R_{17}$ is selected from the group consisting of benzoxazolyl, benzothiazolyl, and indolyl, wherein each group is optionally substituted with from 1 to 2 substituents selected from the group consisting of $CON(R^{20})_2$, $C_{1-3}$ straight or branched alkyl and aryl, wherein the aryl substituents are optionally substituted with 1 substituent selected from the group consisting of $CF_3$; and $R^{20}$ is hydrogen.

11. The compound of claim 10 wherein q=O; and $R_{17}$ is selected from the group consisting of benzoxazolyl, benzothiazolyl, and indolyl, wherein each group is optionally substituted with from 1 to 2 substituents selected from the group consisting of $CON(R^{20})_2$, $C_{1-3}$ straight or branched alkyl and aryl, wherein the aryl substituents are optionally substituted with 1 substituent selected from the group consisting of $CF_3$.

12. A substituted piperazine compound having the following formula:

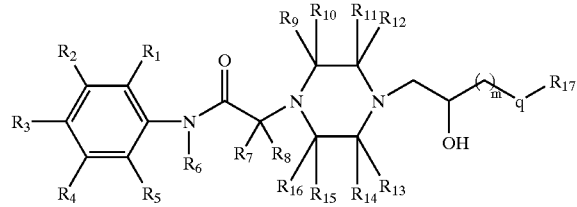

wherein q=O:

m=1, 2 or 3;

$R_1$, $R_2$, $R_3$, $R_4$ and $R_5$ are each independently selected from the group consisting of hydrogen, $OR^{20}$ and $C_{1-2}$ alkyl;

$R_6$, $R_7$ and $R_8$ are each hydrogen;

$R_9$, $R_{10}$, $R_{11}$, $R_{12}$, $R_{13}$, $R_{14}$, $R_{15}$ and $R_{16}$ are each independently selected from the group consisting of hydrogen and $C_{1-2}$ alkyl, or wherein $R_9$ and $R_{10}$ may together form a carbonyl;

$R_{17}$ is selected from the group consisting of benzoxazolyl, benzothiazolyl, and indolyl, wherein each group is optionally substituted with 1 substituent selected from the group consisting of $CON(R^{20})_2$, $C_{1-3}$ straight or branched alkyl, and aryl, wherein the aryl substituents are optionally substituted with 1 substituent selected from the group consisting of $CF_3$; and $R^{20}$ is hydrogen.

13. The compound of claim 12 wherein $R_{17}$ is a benzothiazolyl group that is optionally substituted with 1 substituent selected from the group consisting of hydrogen, $CON(R^{20})_2$, $C_{1-3}$ straight or branched alkyl, and aryl, wherein the aryl substituents are optionally substituted with 1 a substituent selected from the group consisting of $CF_3$.

14. The compound of claim 12 wherein $R_{17}$ is a benzothiazolyl group that is optionally substituted at the 2-position with 1 substituent selected from the group consisting of hydrogen, methyl and phenyl.

15. The compound of claim 12 wherein $R_{17}$ is a benzothiazol-5-yl group that is optionally substituted with 1 substituent selected from the group consisting of $CON(R^{20})_2$, $C_{1-3}$ straight or branched alkyl and aryl, wherein the aryl substituents are optionally substituted with 1 substituent selected from the group consisting of $CF_3$, $R^{20}$ is hydrogen.

16. A compound of claim 12 wherein $R_{17}$ is a benzothiazol-5-yl group that is optionally substituted at the 2-position with 1 substituent selected from the group consisting of hydrogen, methyl and phenyl; and $R^{20}$ is hydrogen.

17. A compound of claim 12 wherein q=O;

$R_1$, $R_2$, $R_3$, $R_4$ and $R_5$ are each independently selected from the group consisting of hydrogen, $OR^{20}$ and methyl;

$R_6$, $R_7$ and $R_8$ are each hydrogen;

$R_{11}$ and $R_{13}$ are each selected from the group consisting of hydrogen and methyl;

$R_9$, $R_{10}$, $R_{12}$, $R_{13}$, $R_{14}$ and $R_{16}$ are each hydrogen or $R_9$ and $R_{10}$ may together form a carbonyl;

$R_{17}$ is that is substituted at the 2-position with methyl; and
$R^{20}$ is hydrogen.

18. A compound of claim 12 wherein q=O;
$R_1, R_2, R_3, R_4$ and $R_5$ are each independently selected tom the group consisting of hydrogen, $OR^{20}$ and methyl;
$R_6, R_7$ and $R_8$ are each hydrogen;
$R_{11}$ and $R_{13}$ are each selected from the group consisting of hydrogen and methyl;
$R_9, R_{10}, R_{12}, R_{14}, R_{15}$ and $R_{16}$ are each hydrogen or $R_9$ and $R_{10}$ may together form a carbonyl;
$R_{17}$ is a benzothiazol-5-yl group that is substituted at the 2-position with phenyl; and
$R^{20}$ is hydrogen.

19. A compound of claim 6 or 7 or 8 or 9 or 10 or 11 or 12 or 13 or 14 or 15 or 16 wherein $R_{17}$ is a benzothiazol-5-yl group that is substituted at the 2-position with methyl.

20. A compound of claim 6 or 7 or 8 or 9 or 10 or 11 or 12 or 13 or 14 or 15, or 16 wherein $R_{17}$ is a benzothiazol-5-yl group that is substituted at the 2-position with phenyl.

21. The compound of claim 1 wherein $R_{17}$ is selected from the group consisting of quinoxalinyl, quinolinyl and isoquinolinyl, wherein each group is optionally substituted with from 1 to 3 substituents selected from the group consisting of hydrogen and $C_{1-15}$ straight or branched alkyl.

22. The compound of claim 21 wherein q=O;
$R_1, R_2, R_3, R_4$ and $R_5$ are each independently selected from the group consisting of hydrogen and $C_{1-8}$ straight or branched alkyl;
$R_6, R_7$ and R are each independently hydrogen; and
$R_9, R_{10}, R_{11}, R_{12}, R_{13}, R_{14}, R_{15}$ and $R_{16}$ are each independently hydrogen.

23. A substituted piperazine compound having the following formula;

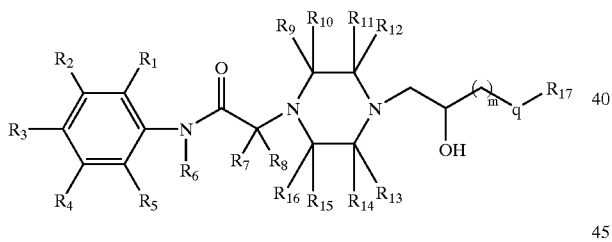

wherein q=O;
m=1, 2, or 3
$R_1, R_2, R_3, R_4$ and $R_5$ are each independently selected from the group consisting of hydrogen and $C_{1-5}$ straight or branched alkyl;
$R_6, R_7$ and $R_8$ are each independently hydrogen;
$R_9, R_{10}, R_{11}, R_{12}, R_{13}, R_{14}, R_{15}$ and $R_{16}$ are each independently hydrogen; and
$R_{17}$ is selected from the group consisting of quinoxalinyl, quinolinyl and isoquinolinyl, wherein each group is optionally substituted with from 1 to 2 substituents selected from the group consisting of and $C_{1-8}$ straight or branched alkyl.

24. The compound of claim 23 wherein q=O;
$R_1, R_2, R_3, R_4$ and $R_5$ are each independently selected from the group consisting of hydrogen, $OR^{20}$ and methyl;
$R_6, R_7$ and $R_8$ are each hydrogen;
$R_9, R_{10}, R_{11}, R_{12}, R_{13}, R_{14}, R_{15}$ and $R_{16}$ are each independently hydrogen; and
$R_{17}$ is selected from the group consisting of quinoxalinyl, quinolinyl and isoquinolinyl, wherein each group is optionally substituted with methyl.

25. The compound of claim 24 wherein q=O;
$R_1, R_2, R_3, R_4$ and $R_5$ are each independently selected from the group consisting of hydrogen and methyl;
$R_6, R_7$ and $R_8$ are each hydrogen;
$R_9, R_{10}, R_{11}, R_{12}, R_{13}, R_{14}, R_{15}$ and $R_{16}$ are each hydrogen; and
$R_{17}$ is selected from the group consisting of quinoxalinyl, quinolinyl and isoquinolinyl, wherein each group is optionally substituted with methyl.

26. The compound of claim 1 wherein $R_{17}$ is a pyridinyl group.

27. The compound of claim 26 wherein q=O;
$R_1, R_2, R_3, R_4$ and $R_5$ are each independently selected from the group consisting of hydrogen and $C_{1-8}$ straight or branched alkyl;
$R_6, R_7$ and $R_8$ are each independently hydrogen;
$R_9, R_{10}, R_{11}, R_{12}, R_{13}, R_{14}, R_{15}$ and $R_{16}$ are each independently hydrogen,
$R_{17}$ is a pyridinyl group.

28. A substituted piperazine compound having the following formula:

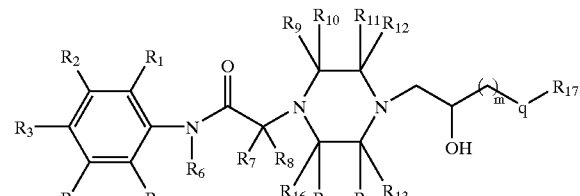

wherein q=O;
m=1, 2 or 3;
$R_1, R_2, R_3, R_4$ and $R_5$ are each independently selected from the group consisting of hydrogen and $C_{1-5}$ straight or branched alkyl;
$R_6, R_7$ and $R_8$ are each independently hydrogen;
$R_9, R_{10}, R_{11}, R_{12}, R_{13}, R_{14}, R_{15}$ and $R_{16}$ are each independently hydrogen; and
$R_{17}$ is a pyridinyl group.

29. The compound of claim 28 wherein q=O;
$R_1, R_2, R_3, R_4$ and $R_5$ are each independently selected from the group consisting of hydrogen and methyl;
$R_6, R_7$ and $R_8$ are each hydrogen;
$R_9, R_{10}, R_{11}, R_{12}, R_{13}, R_{14}, R_{15}$ and $R_{16}$ are each independently hydrogen; and
$R_{17}$ is a pyridinyl group.

30. The compound of claim 10 wherein q=NH; and
$R_{17}$ is selected from the group consisting of benzoxazolyl, benzothiazolyl, and indolyl.

31. A substituted piperazine compound having the following formula:

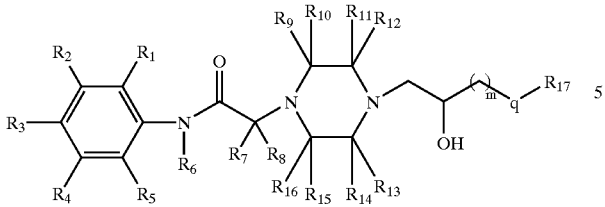

wherein q=NH;
m=1, 2, or 3;
$R_1$, $R_2$, $R_3$, $R_4$ and $R_5$ are each independently selected from the group consisting of hydrogen and $C_{1-2}$ alkyl;
$R_6$, $R_7$ and $R_8$ are each hydrogen;
$R_9$, $R_{10}$, $R_{11}$, $R_{12}$, $R_{13}$, $R_{14}$, $R_{15}$ and $R_{16}$ are each independently hydrogen; and
$R_{17}$ is selected from the group consisting of benzothiazolyl and benzoxazolyl, wherein each group is optionally substituted with 1 substituent selected from the group consisting of $C_{1-3}$ straight or branched alkyl.

32. A substituted piperazine compound having the following formula:

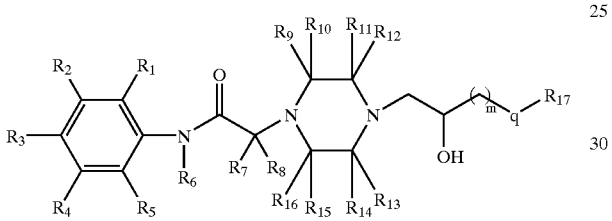

wherein q=NH;
m=1, 2, or 3;
$R_1$, $R_2$, $R_3$, $R_4$ and $R_5$ are each independently selected from the group consisting of hydrogen and methyl;
$R_6$, $R_7$ and $R_8$ are each hydrogen;
$R_9$, $R_{10}$, $R_{11}$, $R_{12}$, $R_{13}$, $R_{14}$, $R_{15}$ and $R_{16}$ are each hydrogen; and
$R_{17}$ is selected from the group consisting of benzothiazolyl and benzoxazolyl, wherein each group is optionally substituted with methyl.

33. A compound selected from the group consisting of
N-(2,6-dimethyl-phenyl)-2-(4-{2-hydroxy-3-[2-(3-trifluoromethylphenyl)-benzoxazol-5-yloxy]-propyl}-piperazin-1-yl)acetamide,
2-{4-[3-(benzothiazol-2-yloxy)-2-hydroxy-propyl]-piperazin-1-yl}-N-(2,6-dimethylphenyl)acetamide,
N-(2,6-dimethylphenyl)-2-{4-[2-hydroxy-3-(2-methyl-benzothiazol-5-yloxy)-propyl]-piperazin-1-yl}acetamide,
4-(3-{4-[(2,6-dimethylphenylcarbamoyl)-methyl]-piperazin-1-yl}-2-hydroxy-propoxy)-1H-indole-2-carboxylic acid amide;2-{4-[3-(benzothiazol-6-yloxy) 2-hydroxy-propyl]-piperazin-1-yl}-N-(2,6-dimethyl-phenyl)-acetamide,
N-(2,6-dimethylphenyl)-2-{4-[2-hydroxy-3-(2-methyl-benzothiazol-6-yloxy)-propyl]-piperazin-1-yl}aceamide,
N-(2,6-dimethylphenyl)-2-{4-[2-hydroxy-3-(2-methyl-benzothiazol-5-yloxy)-propyl]-3,5-dimethyl-piperazine-1-yl}acetamide,
2-{4-[2-hydroxy-3-(2-methyl-benzothiazol-5-yloxy)-propyl]-piperazin-1-yl}-N-(4-hydroxy-phenyl)acetamide,
N-(2,6-dimethylphenyl)-2-{4-[2-hydroxy-3-(2-phenyl-benzothiazol-5-yloxy)-propyl]-piperazin-1-yl}acetamide,
N-(2,6-dimethylphenyl)-2-{4-[2-hydroxy-3-(2-phenyl-benzoxazol-5-yloxy)-propyl]-piperazin-1-yl}acetamide,
N-(2,6-dimethylphenyl)2-{4-[2-hydroxy-3-(2-phenyl-benzothiazol-7-yloxy)-propyl]-piperazin-1-ylacetamide,
N-(2,6-dimethylphenyl)-2-{4-[2-hydroxy-3-(2-methyl-benzothiazol-5-yloxy)-propyl]-2-oxo-piperazin-1-yl}acetamide,
N-(2,6-dimethylphenyl)-2-{4-[2-hydroxy-3-(2-methyl-benzoxazol-5-yloxy)-propyl]-piperazin-1-yl}acetamide,
N-(2,6-dimethylphenyl)-2-(4-{2-hydroxy-3-[2-(4-trifluoromethyl-phenyl)-benzoxazol-5-yloxy]-propyl}-piperazin-1-yl)acetamide,
N-(2,6-dimethylphenyl)-2-{4-[2-hydroxy-3-(quinoxalin-2-yloxy)-propyl]-piperazin-1-yl}acetamide,
N-(2,6-dimethylphenyl)-2-{4-[2-hydroxy-3-pyridin-3-yloxy)-propyl]-piperazin-1-yl}acetamide,
N-(2,6-dimethylphenyl)-2-{4-[2-hydroxy-3-(quinolin-4-yloxy)-propyl]-piperazin-1-yl}acetamide,
N-(2,6-dimethylphenyl)-2-{4-[2-hydroxy-3-(isoquinolin-5-yloxy)-propyl]-piperazin-1-yl}acetamide,
N-(2,6-dimethylphenyl)-2-{4-[2-hydroxy-3-(quinolin-6-yloxy)-propyl]-piperazin-1-yl}acetamide,
N(2,6-dimethylphenyl)-2-{4-[2-hydroxy-3-(2-methyl-quinolin-7-yloxy)-propyl]-piperazin-1-yl}acetamide,
2-{4-[3-(benzothiazol-2-ylamino)-2-hydroxypropyl] piperazinyl}-N-(2,6-dimethylphenyl)acetamide, and
2-{4-[3-(benzoxazol-2-ylamino)-2-hydroxypropyl] piperazinyl}-N-(2,6-dimethylphenyl)acetamide.

34. A method of treatment comprising administering a therapeutically effective amount of a compound of claim 1 to a mammal in need of a treatment selected from the group consisting of protecting skeletal muscles against damage resulting from trauma, protecting skeletal muscles subsequent to muscle or systemic diseases, treating shock conditions, preserving donor tissue and organs used in transplants, and treating cardiovascular diseases.

35. The method of claim 34 wherein the cardiovascular disease is selected from the group consisting of atrial and ventricular arrhythmias, Prinzmetal's (variant) angina, stable angina, exercise induced angina, congestive heart disease, and myocardial infarction.

36. The method of claim 34 or 35 wherein the therapeutically effective amount ranges from about 0.01 to about 100 mg/kg weight of the mammal.

37. The method of claim 34 or 35 wherein the mammal is a human.

38. A pharmaceutical composition comprising a compound of claim 1 and one or more pharmaceutical excipients.

39. The pharmaceutical composition of claim 38 wherein the pharmaceutical composition is in the form of a solution.

40. The pharmaceutical composition of claim 38 wherein the pharmaceutical composition is in a form selected from the group consisting of a tablet and a capsule.

41. A method of preserving donor tissue and organs used in transplants, comprising administering to a mammal in need thereof a therapeutically effective dose of a compound of claim 1.

* * * * *

UNITED STATES PATENT AND TRADEMARK OFFICE
CERTIFICATE OF CORRECTION

PATENT NO.   : 6,573,264 B1
DATED        : June 3, 2003
INVENTOR(S)  : Zablocki et al.

It is certified that error appears in the above-identified patent and that said Letters Patent is hereby corrected as shown below:

Column 50,
Lines 14 and 66, delete "$OR_{20}$" and replace with -- $OR^{20}$ --.
Line 59, delete $CON(R_{20})_2$" and replace with -- $CON(R^{20})_2$ --.

Column 51,
Line 29, delete "$CON(R_{20})_2$" and replace with -- $CON(R^{20})_2$ --.

Column 53,
Line 4, delete "tom" and replace with -- from --.

Signed and Sealed this

Seventh Day of October, 2003

JAMES E. ROGAN
*Director of the United States Patent and Trademark Office*